(12) United States Patent
Wende et al.

(10) Patent No.: US 9,040,243 B2
(45) Date of Patent: May 26, 2015

(54) METHOD FOR DETECTING AND/OR QUANTIFYING HUMAN DNA

(75) Inventors: Andy Wende, Hilden (DE); Francesca Dipasquale, Dusseldorf (DE); Sabine Werner, Dusseldorf (DE); Sascha Strauss, Solingen (DE)

(73) Assignee: QIAGEN GMBH, Hilden (DE)

( * ) Notice: Subject to any disclaimer, the term of this patent is extended or adjusted under 35 U.S.C. 154(b) by 27 days.

(21) Appl. No.: 13/825,226

(22) PCT Filed: Sep. 22, 2011

(86) PCT No.: PCT/EP2011/066500
§ 371 (c)(1),
(2), (4) Date: May 7, 2013

(87) PCT Pub. No.: WO2012/038503
PCT Pub. Date: Mar. 29, 2012

(65) Prior Publication Data
US 2013/0224742 A1 Aug. 29, 2013

(30) Foreign Application Priority Data
Sep. 23, 2010 (EP) .................................... 10178914

(51) Int. Cl.
*C12Q 1/68* (2006.01)
*C12P 19/34* (2006.01)

(52) U.S. Cl.
CPC ............ *C12Q 1/6853* (2013.01); *C12Q 1/6851* (2013.01); *C12Q 1/6846* (2013.01); *C12Q 1/686* (2013.01); *C12Q 1/6865* (2013.01)

(58) Field of Classification Search
CPC ... C12Q 1/6846; C12Q 1/6851; C12Q 1/6865
See application file for complete search history.

(56) References Cited

U.S. PATENT DOCUMENTS

| | | |
|---|---|---|
| 2006/0099620 A1 | 5/2006 | Walker et al. |
| 2006/0147944 A1* | 7/2006 | Chomczynski ................ 435/6 |
| 2012/0087862 A1* | 4/2012 | Hood et al. .................. 424/9.1 |

FOREIGN PATENT DOCUMENTS

WO    WO 2008/021290 A2    2/2008

OTHER PUBLICATIONS

Liu et al. Comprehensive analysis of the pseudogenes of glycolytic enzymes in vertebrates: the anomalously high number of GAPDH pseudogenes highlights a recent burst of retrotrans-positional activity. BMC Genomics (2009) 10:480, pp. 1-12.*
Walker, et al., "Human DNA quantitation using Alu element-based polymerase chain reaction", Analytical Biochemistry, vol. 315, No. 1, Apr. 1, 2003, pp. 122-128.
Foran, "Relative degradation of nuclear and mitochondrial DNA: an experimental approach", Journal of Forensic Sciences, vol. 51, No. 4, Jul. 2006, pp. 766-770.
"*Homo sapiens* chromosome 5 clone XXcos-B22C85, complete sequence", Dec. 13, 2002, XP002627313, retrieved from EBI accession No. EMBL: AC138035; Data accession No AC138035 compound.
"*Homo sapiens* chromosome 16 clone XXcos-y2118C7, complete sequence", Dec. 4, 2002, XP002627314, retrieved from EBI accession No. EMBL: AC137817; Database accession No. AC137817 compound.
"*Homo sapiens* cosmid clone XXcos-2185C13 from 7, complete sequence", Feb. 27, 2002, XP002627315, retrieved from EBI accession No. EMBL: AC112517, Database accession No. AC112517 compound.
"*Homo sapiens* cosmid clone XXcos-2185C4 from 7, complete sequence", Oct. 24, 2001, XP002663891, retrieved from EBI accession No. EM_HUM: AC097645, Database accession No. AC097645 sequence.
"*Homo sapiens* chromosome 17 clone RP11-949L12 map 17, *Sequencing in Progress*, 10 unordered pieces", Aug. 16, 2002, XP002663892, retrieved from EBI accession No. EM_HTG: AC130290, Database accession No. AC130290 sequence.
"*Homo sapiens* BAC clone RP11-304M2 from 11, complete sequence", May 26, 2000, XP002663893, retrieved from EBI accession No. EM_HUM: AC0639287, Database accession No. AC069287 sequence.

* cited by examiner

*Primary Examiner* — Kenneth R. Horlick
*Assistant Examiner* — David Thomas
(74) *Attorney, Agent, or Firm* — Fanelli Haag PLLC

(57) ABSTRACT

The present invention relates to a method, kit and use of various nucleic acid sequences for deleting and/or quantifying one or more nucleic acids of a genome in a sample. Wherein the nucleic acid is amplified and the locus that is amplified is a multi copy locus within the genome, the multicopy locus has copies on at least two different chromosomes and the amplification product is detected and/or quantified.

40 Claims, 17 Drawing Sheets

Fig. 1 (continued)

Figure 1:
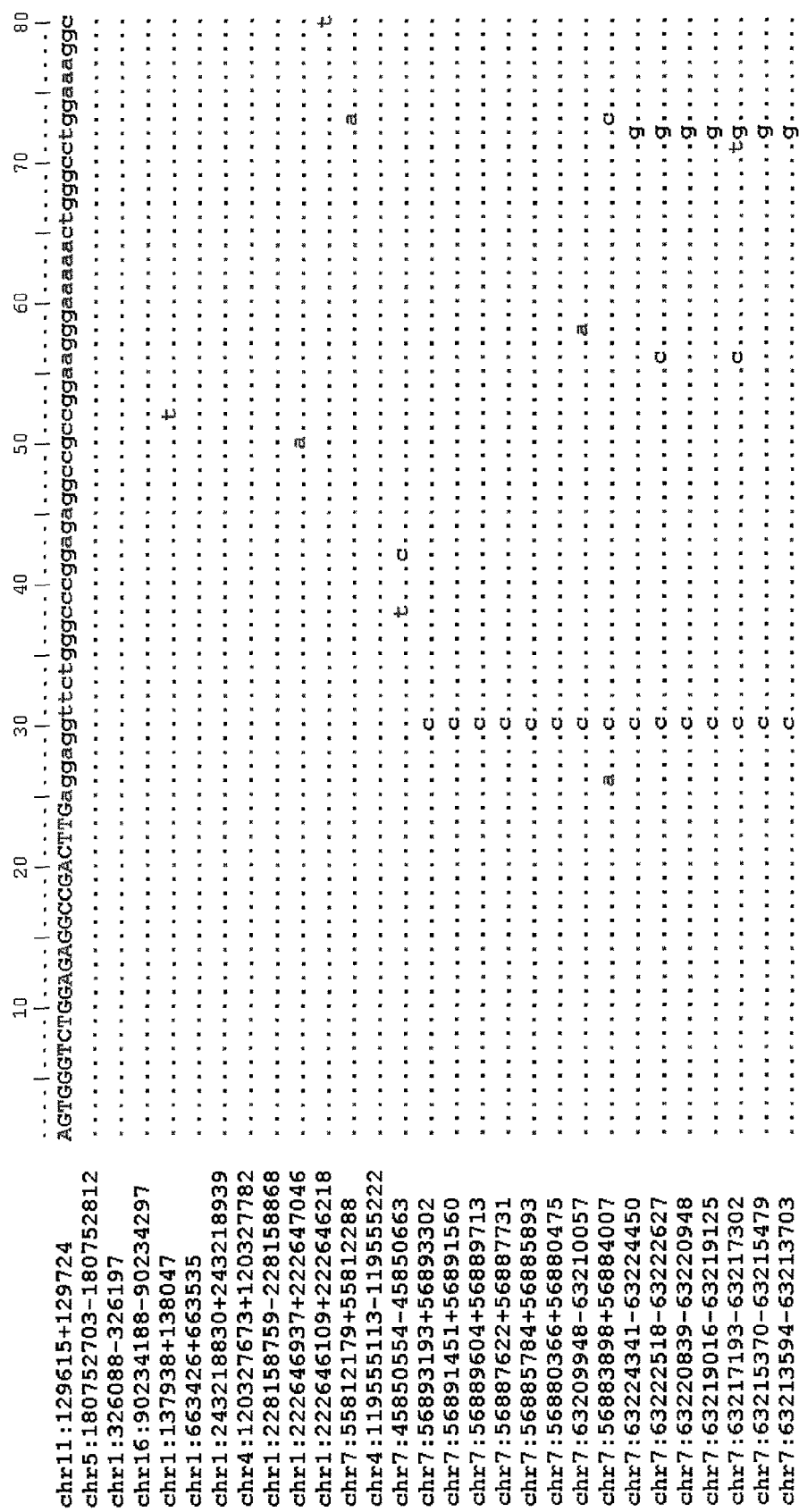

```
                                              90        100       110
                                      ....|....|....|....|....|....|
chr11:129615+129724                   cgttgtcAGGAATGAGCCCCATGGGCCTGA
chr5:180752703-180752812              ..............................
chr1:326088-326197                    ..............................
chr16:90234188-90234297               ..............................
chr1:137938+138047                    ..............................
chr1:663426+663535                    t.............................
chr1:243218830+243218939              ......g.......................
chr4:120327673+120327782              ......g.......................
chr1:228158759-228158868              ......g.......................
chr1:222646937+222647046              ......g.......................
chr1:222646109+222646218              t.....g.......................
chr7:55812179+55812288                ......g.......................
chr4:119555113-119555222              t.....g.......................
chr7:45850554-45850663                ......g.......................
chr7:56893193+56893302                ......g.......................
chr7:56891451+56891560                ......g.......................
chr7:56889604+56889713                ......g.......................
chr7:56887622+56887731                ......g.......................
chr7:56885784+56885893                ......g.......................
chr7:56880366+56880475                ......g.......................
chr7:63209948-63210057                ......g.......................
chr7:56883898+56884007                ......g.......................
chr7:63224341-63224450                ......g.......................
chr7:63222518-63222627                ......g.......................
chr7:63220839-63220948                ......g.......................
chr7:63219016-63219125                ......g.......................
chr7:63217193-63217302                ......g.......................
chr7:63215370-63215479                ......g.......................
chr7:63213594-63213703                ......g.......................
```

Fig. 6

| SEQ ID NO. 1 target sequence | 5'-TCAACAGGCCACCGTGAGGGAGGAGCTGGGCCGCACGCGGGCTGCTGGGAGG CAGGCAGGGACTTGGCCCCGAGAGGCCGCCGTGGGGGCAAGAGCTGGGCCTG GAGAGGCCCCTGGGAGGCAAGGGCGGGGCCTGCAGAGGCTGTTCTCCAACCA GTGCTAGAACTGTACAGGCCACCAGGAGGCAGGAGGTGGGCCCCTCAGAGCTT GGCTGGAGAAAGTTCGGGGCCTACAAAGCGGTTGGGAGCTGGCCAGGAGTT GAGCCAAAAGAGCTTGCTTACTTGCTGGGAGGCAGGGCCGGGAGAGCCCGAC TTCAGGACAACTTGGGCCTGCGGCAGTCGCCGGGAGGCCCAACCTTGGCGTG GAGGAGCCCACCGACCGGAGACCATTTGGGGCCTGGAGATGCCATCGGAGGG CAGGAGCTCATCCTGGAGAGGCCACCGTGAGGCCTGACCTGGGCCTGGGGAG CTTGGCTTGAGGAAGCTGTGGGCCGACCAAGGCCGCCAGGAGATGGGTAGGC ACTGAGTCCAAAGAGGTTGTTGAGAGGCAGGAATCGGGCCTGGAGACCCAAC CAGGAAGAAGAGCTGGGCCCGGAGAGAATGCACGGAGGGTGCAAGTGGGTCT GGAGAGGCCGACTTGAGGAGGTTCTGGGCCCGGAGAGGCCGCCGGAAGGGAA AAACTGGGCCTGGAAAGGCCGTTGTCAGGAATGAGCCCCATGGGCCTGAAGA GGCCACTGGCAGGCGGGAGCTGGGCCTGCCGAAGCGGCCGAGAGGCAGGAGC TTTGGACTCGGGAGGCCGCAGTGAAGCAACAGCTAGCTGGGCGTGGAGAGTC CGCTGTGAGGCAGAGGCTGGGCCTGTGCAGGCCTTCGGGGAGGCAGGAGGCTG GGCCTTGTCGAGGCCTGCAGAGGCCACCGAAAGTCAAAAGCGGGGCTTGGGA AGGCCGCCGGGAGGCATGAGCTGGGCTGGGCCGAAAGAGGCCACTGGGAGGC AGGAGGAGCTGGGCCTGGAGAGGCTGCCAAAAGGCAGGAGCTTCGCCTGAGG ATGCCACAGTGAGACACCATCTGGGTCTGGAGGGTCCACTGTGAGGCAGAGG CTGACCTGTAGAGTCCGACAGTAGACAGAAGTTGGGCAAAAGCCTGATTTGA GGAAGTTTTGGGCTTCAAGAGTCAGCCACGAGGCAGGCACTAGGCCTGGAAA TGGCCTCACAGTCATGAGTTGGGCCTAAATGGGCCACTGTGAGGGAGGAGCT GTGCCTGTTGAGGCTGCTGGCAGGCAGGCAGAAATTTGGCCTGGGGCAGCTG CCATGAGGCAAGAGCTGGGCCTGGAAAAAGCCCCTGGGAGGCAAGAGCAGGG CCTGCAGAGGCTGTTCTCAAGTCAAAGCTGGGCCTGTTGATGCCACCGGGAA GCAGAAGGTGGGCCTGGAGAGTTTGACTTGAGGAAGTTTTGGGCCTACATTG GCCGCCATGAGCTGGACAGGAACTGGGCCAAAAAAGGCTGTTGTGAGGCAGC AGTTGTGCCTGTAGACCCAGCCAAGAGGAAGAGGTGGGTCTGGAGAAGCCCC CATGAGGCAGAGGTTGGGCCTGTAGACTCTGACAGGAGGCAGGAGCTGGGCC TGGACAGGTCAACTTGAGGAGATTTTGGGCCTTCATAGGCCACCAGGAGGCA GTAGTTGGGACTAGAGAGTCTGACTTGAGTAAGTTTTGGGCCCGGAGATGAC GTCCTGGGACAGGAGTTGGGCGTGGAGAGGCCACCGTGAGGCATAAGCTGGA TGTAGAGAGGCCAGTGTGAGGCAAGACCTGGGCCTGTCTAGGCTGCTGGGAG ACAGGCAGGAATCTGGCCAGGGAAGGTTGCCATGAGACAAAAGTTGGGCCTG GAAAGGCCCTTGTGAAGCATGAGCTTGGCCTAAAGAGGCCACTGGGTGGCAG GAGCTGGGTGTGTAGAAGCTGCTGAAAGCTTGGGAGCTTGGCTTGGGCGGTC CACAGTGAGGTAGATGCTGGGCGT-3' |
| SEQ ID NO. 2 hT-For1 (primer) | 5'-AGTGGGTCTGGAGAGGCCGACTTG-3' |
| SEQ ID NO. 3 hT-Rev1 (primer) | 5'-TCAGGCCCATGGGGCTCATTCCT-3' |
| SEQ ID NO. 4 hT-Pro1 (probe) | 5'-FAM-TTCTGGGCCCGGAGAGGCCGC-BHQ1-3' |
| SEQ ID NO. 5 hT-For2 (primer) | 5'-GCAGAAGGTGGGCCTGGAGAGTTTGAC-3' |

Fig. 6 (continued)

| | |
|---|---|
| SEQ ID NO. 6<br>hT-Rev2<br>(primer) | 5'-CCTTTTTTGGCCCAGTTCCTGTCCAGC-3' |
| SEQ ID NO. 7<br>hT-Pro2 (probe) | 5'-FAM-GGAAGTTTTGGGCCTACATTGGCCGCCATG-BHQ1-3' |
| SEQ ID NO. 8<br>hT-For3<br>(primer) | 5'-AAGGTGGGCCTGGAGAGTTT-3' |
| SEQ ID NO. 9<br>hT-Rev3<br>(primer) | 5'-CCTTTTTTGGCCCAGTTCCTGT-3' |
| SEQ ID NO. 10<br>hT-Pro3 (probe) | 5'-HEX-AAGTTTTGGGCCTACATTGGCCGC-BHQ1-3' |
| SEQ ID NO. 11<br>4NS1C Scorpion | 5'-Fam-CGAGCTCAGTTCTGCCTGTAGAGCTCG-dabcyl-C18-<br>ACCTCTTCCTCTTGGCTGGG |
| SEQ ID NO. 12<br>4NS1C primer | 5'-CCGGGAAGCAGAAGGTGG-3' |
| SEQ ID NO. 13<br>(Chr. 11) | AGTGGGTCTGGAGAGGCCGACTTGaggaggttctgggcccggagaggccgcc<br>ggaagggaaaaactgggcctggaaaggccgttgtcAGGAATGAGCCCCATGG<br>GCCTGA |
| SEQ ID NO. 14<br>(Chr. 5) | AGTGGGTCTGGAGAGGCCGACTTGaggaggttctgggcccggagaggccgcc<br>ggaagggaaaaactgggcctggaaaggccgttgtcAGGAATGAGCCCCATGG<br>GCCTGA |
| SEQ ID NO. 15<br>(Chr. 1) | AGTGGGTCTGGAGAGGCCGACTTGaggaggttctgggcccggagaggccgcc<br>ggaagggaaaaactgggcctggaaaggccgttgtcAGGAATGAGCCCCATGG<br>GCCTGA |
| SEQ ID NO. 16<br>(Chr. 16) | AGTGGGTCTGGAGAGGCCGACTTGaggaggttctgggcccggagaggccgcc<br>ggaagggaaaaactgggcctggaaaggccgttgtcAGGAATGAGCCCCATGG<br>GCCTGA |
| SEQ ID NO. 17<br>(Chr. 1) | AGTGGGTCTGGAGAGGCCGACTTGaggaggttctgggcccggagaggccgct<br>ggaagggaaaaactgggcctggaaaggccgttgtcAGGAATGAGCCCCATGG<br>GCCTGA |
| SEQ ID NO. 18<br>(Chr. 1) | AGTGGGTCTGGAGAGGCCGACTTGaggaggttctgggcccggagaggccgcc<br>ggaagggaaaaactgggcctggaaaggctgttgtcAGGAATGAGCCCCATGG<br>GCCTGA |
| SEQ ID NO. 19<br>(Chr. 1) | AGTGGGTCTGGAGAGGCCGACTTGaggaggttctgggcccggagaggccgcc<br>ggaagggaaaaactgggcctggaaaggccgttgtgAGGAATGAGCCCCATGG<br>GCCTGA |
| SEQ ID NO. 20<br>(Chr. 4) | AGTGGGTCTGGAGAGGCCGACTTGaggaggttctgggcccggagaggccgcc<br>ggaagggaaaaactgggcctggaaaggccgttgtgAGGAATGAGCCCCATGG<br>GCCTGA |
| SEQ ID NO. 21<br>(Chr. 1) | AGTGGGTCTGGAGAGGCCGACTTGaggaggttctgggcccggagaggccgcc<br>ggaagggaaaaactgggcctggaaaggccgttgtgAGGAATGAGCCCCATGG<br>GCCTGA |
| SEQ ID NO. 22<br>(Chr. 1) | AGTGGGTCTGGAGAGGCCGACTTGaggaggttctgggcccggagaggccacc<br>ggaagggaaaaactgggcctggaaaggccgttgtgAGGAATGAGCCCCATGG<br>GCCTGA |
| SEQ ID NO. 23<br>(Chr. 1) | AGTGGGTCTGGAGAGGCCGACTTGaggaggttctgggcccggagaggccgcc<br>ggaagggaaaaactgggcctggaaaggttgttgtgAGGAATGAGCCCCATGG<br>GCCTGA |

Fig. 6 (continued)

| SEQ ID NO. 24 (Chr. 7) | AGTGGGTCTGGAGAGGCCGACTTGaggaggttctgggcccggagaggccgccggaagggaaaaactgggcctagaaaggccgttgtgAGGAATGAGCCCCATGGGCCTGA |
|---|---|
| SEQ ID NO. 25 (Chr. 4) | AGTGGGTCTGGAGAGGCCGACTTGaggaggttctgggcccggagaggccgccggaagggaaaaactgggcctggaaaggctgttgtgAGGAATGAGCCCCATGGGCCTGA |
| SEQ ID NO. 26 (Chr. 7) | AGTGGGTCTGGAGAGGCCGACTTGaggaggttctgggtccgcagaggccgccggaagggaaaaactgggcctggaaaggccgttgtgAGGAATGAGCCCCATGGGCCTGA |
| SEQ ID NO. 27 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 28 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 29 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 30 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 31 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 32 (Chr. 7) | AGTGGGTCTGGAGAGGCCGACTTGaggagcttctgggcccggagaggccgccggaagggaaaaactgggcctggaaaggccgttgtgAGGAATGAGCCCCATGGGCCTGA |
| SEQ ID NO. 33 (Chr. 7) | AGTGGGTCTGGAGAGGCCGACTTGaggagcttctgggcccggagaggccgccggaagagaaaaactgggcctggaaaggccgttgtgAGGAATGAGCCCCATGGGCCTGA |
| SEQ ID NO. 34 (Chr. 7) | AGTGGGTCTGGAGAGGCCGACTTGaagagcttctgggcccggagaggccgccggaagggaaaaactgggcctcgaaaggccgttgtgAGGAATGAGCCCCATGGGCCTGA |
| SEQ ID NO. 35 (Chr. 7) | AGTGGGTCTGGAGAGGCCGACTTGaggagcttctgggcccggagaggccgccggaagggaaaaactgggccgggaaaggccgttgtgAGGAATGAGCCCCATGGGCCTGA |
| SEQ ID NO. 36 (Chr. 7) | AGTGGGTCTGGAGAGGCCGACTTGaggagcttctgggcccggagaggccgccggacgggaaaaactgggccgggaaaggccgttgtgAGGAATGAGCCCCATGGGCCTGA |
| SEQ ID NO. 37 (Chr. 7) | AGTGGGTCTGGAGAGGCCGACTTGaggagcttctgggcccggagaggccgccggaagggaaaaactgggccgggaaaggccgttgtgAGGAATGAGCCCCATGGGCCTGA |
| SEQ ID NO. 38 (Chr. 7) | AGTGGGTCTGGAGAGGCCGACTTGaggagcttctgggcccggagaggccgccggaagggaaaaactgggccgggaaaggccgttgtgAGGAATGAGCCCCATGGGCCTGA |
| SEQ ID NO. 39 (Chr. 7) | AGTGGGTCTGGAGAGGCCGACTTGaggagcttctgggcccggagaggccgccggacgggaaaaactgggctgggaaaggccgttgtgAGGAATGAGCCCCATGGGCCTGA |
| SEQ ID NO. 40 (Chr. 7) | AGTGGGTCTGGAGAGGCCGACTTGaggagcttctgggcccggagaggccgccggaagggaaaaactgggccgggaaaggccgttgtgAGGAATGAGCCCCATGGGCCTGA |

Fig. 6 (continued)

| SEQ ID NO. 41 (Chr. 7) | AGTGGGTCTGGAGAGGCCGACTTGaggagcttctgggcccggagaggccgcc ggaagggaaaaactgggccgggaaaggccgttgtgAGGAATGAGCCCCATGG GCCTGA |
|---|---|
| SEQ ID NO. 42 (chr16:90233371+90233516) | ACCTCTTCCTCTTGGCTGGGtctacaggcacaactgctgcctcacaacagcc ttttttggcccagttcctgtccagctcatggcggccaatgtaggccca aaacttcctcaagtcaaactctccaggcCCACCTTCTGCTTCCCGG |
| SEQ ID NO. 43 (chr1:228156073+228156218) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 44 (chr1:325270+325415) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 45 (chr5:180751885+180752030) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 46 (chr7:128292059+128292204) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCaG |
| SEQ ID NO. 47 (chr11:130397-130542) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 48 (chr1:243219596-243219741) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 49 (chr1:222649519-222649664) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 50 (chr1:664208-664353) | ACCTCTTCCTCTTGGCTGGGtctacaggcacaactgctgcctcacaacag ccttttttggcccagttcctgtccagctcatggcggccaatgtaggccca aaacttcctcaagtcaaactctccaggcCCACCTTCTGCTTCCCGG |
| SEQ ID NO. 51 (chr1:138720-138865) | ACCTCTTCCTCTTGGCTGGGtctacaggcacaactgctgcctcacaacag ccttttttggcccagttcctgtccagctaatggcggccaatgtaggccca aaacttcctcaagtcaaactctccaggcCCACCTTCTGCTTCCCGG |

Fig. 7

```
                1290       1300       1310       1320       1330       1340       1350       1360
           ....|....|....|....|....|....|....|....|....|....|....|....|....|....|....|....|
seq-id 1       AATTTGGCCTGGGGCAGCTGCCATGAGGCAAGAGACTGGGCCTGGAAAAAGCCCCTGGGAGGCAAGAGCAAGGGCCTGCAGA
ampl seq-id 2+3
ampl seq-id 11+12
ampl seq-id 5+6
ampl seq-id 8+9

1370       1380       1390       1400       1410       1420       1430       1440
           ....|....|....|....|....|....|....|....|....|....|....|....|....|....|....|....|
seq-id 1       GGCTGTTCTCAAGTCAAAGCTCAAAAGCTGGGCCCTGTGTTGATGCCACCGGGAAGCAGCAGAAGGTGGGCCTGGAGAGTTTGACTTGAGGAAG
ampl seq-id 2+3                                                           CCGGGAAGCAGAAGGTGGgcctggagagtttgacttgaggaag
ampl seq-id 11+12                                                                 GCAGAAGGTGGGCCTGGAGAGTTTGACttgacttgaggaag
ampl seq-id 5+6                                                                         AAGGTGGGCCTGGAGAGTTTgacttgaggaag
ampl seq-id 8+9
```

Fig. 7 (continued)

```
                     1450       1460       1470       1480       1490       1500       1510       1520
                ....|....|....|....|....|....|....|....|....|....|....|....|....|....|....|....|
seq-id 1        TTTTGGGCCTACATTGGCCGCCATGAGCTGGACAGGAACTGGGCCAAAAAAGGCTGTTGTGAGGCAGCAGTTGTGCCTGT
ampl seq-id 2+3 ttttgggcctacattggccgccatgagctggacaggaactgggccaaaaaaggctgttgtgaggcagcagttgtgcctgt
ampl seq-id 11+12 ttttgggcctacattggccgccatgagctgGACAGGAACTGGGCCAAAAAAGG
ampl seq-id 5+6
ampl seq-id 8+9 ttttgggcctacattggccgccatgagctggACAGGAACTGGGCCAAAAAAGG 1530       1540       1550       1560       1570       1580       1590       1600
                ....|....|....|....|....|....|....|....|....|....|....|....|....|....|....|....|
seq-id 1        AGACCCAGCCAAGAGAGGAAGAGAGGTGGGTCTGGAGAAGCCCCCATGAGGCAGAGGTTGGGCCTGTAGACGCTGACAGGAGGC
ampl seq-id 2+3 agaCCCAGCCAAGAGAGGAAGAGAGGT
ampl seq-id 11+12
ampl seq-id 5+6
ampl seq-id 8+9
```

Fig. 9

| | Short PCR system (146bp) - quantification ng/µl | Large PCR system (363bp) - quantification ng/µl | Ratio Short quant / large quant |
|---|---|---|---|
| 3 Male DNA | 0,64 | 0,64 | 0,99 |
| 4 Male DNA degr. 500bp | 1,15 | 0,56 | 2,05 |
| 5 Male DNA degr. 300bp | 0,91 | 0,25 | 3,59 |
| 6 Male DNA degr. 150bp | 0,33 | 0,01 | 60,68 |

| CNV reference | Copy number, per human genome | Cq change (reference assay) | GOI copy number (real) | GOI copy number (calculated) | CNV calling for GOI |
|---|---|---|---|---|---|
| Type-it CNV reference | 36 | 0 | 2 | 2.00 | NC: Correct |
| | 36+1 | −0.04 | 2 | 1.94 | NC: Correct |
| | 36−1 | +0.04 | 2 | 2.06 | NC: Correct |
| Single-copy gene | 2 | 0 | 2 | 2.00 | NC: Correct |
| | 2+1 | −0.58 | 2 | 1.33 | Loss: False |
| | 2−1 | +1 | 2 | 4.00 | Gain: False |

METHOD FOR DETECTING AND/OR QUANTIFYING HUMAN DNA

This application is a National Stage of PCT/EP2011/066500, filed Sep. 22, 2011 which claims priority to European Application No. 10178914.7, filed Sep. 23, 2010, the disclosures of which are incorporated herein by reference in their entirety.

The instant application contains a Sequence Listing which has been submitted in ASCII format via EFS-Web and is hereby incorporated by reference in its entirety. Said ASCII copy, created on Mar. 20, 2013, is named 0051_0076_USI_Sequence_Listing.txt and is 22050 bytes in size.

FIELD OF THE INVENTION

The present invention is in the field of molecular biology, diagnostics, more particularly in the field of analytical and forensic sciences. The invention is further in the field of nucleic acid amplification and quantification, more particularly in the field of DNA quantification.

BACKGROUND

The determination of the quantity of DNA recovered from forensic samples as well as other samples is a critical step in the over all DNA typing process, but also in the detection of DNA in various other fields of science. A narrow range of input DNA from 0.5 to 2 ng is often needed to produce optimal results with for example multiplex DNA typing kits. Therefore, in order to ensure that a positive result is a positive result and/or a negative result is a negative result due to the absence of DNA, quantification of DNA is of absolute importance. Furthermore, the quality of standards for forensic DNA testing laboratories requires human-specific DNA quantification. This is due to isolation techniques that can recover human DNA as well as bacterial and other exogenous DNA. A number of procedures have been developed to permit quantification of human-specific DNA including start-blot techniques, liquid based hybridization assays and real-time PCR (polymerase chain reaction). Currently, real-time PCR is the dominant technique due to its wide dynamic range and ease of automation.

The modern STR-Kits have become much more sensitive and can obtain good results even using low amounts of DNA. Therefore, there is a desire for a method, kit and nucleic acid region that allows precise and accurate quantification of human DNA even in low concentrated samples. There are certain quantification and detection kits already available, however, these have serious drawbacks. One such kit is the Quantifiler Human Kit (Applied Biosystems) another kit is the Quantifiler Duo Kit (Applied Biosystems) another kit is the Plexor HY Real-Time PCR Quantification Kit (Promega). Both the Quantifiler Duo Kit and the Plexor HY Kit target an autosomal and a gonosomal (Y-chromosome) target on the genome.

Drawbacks for the kits: According to LaSalle et al., (Forensic Science International: Genetics, "Analysis of Single and Multi-copy Methods for DNA Quantification by Real-Time Polymerase Chain Reaction") the Quantifier Kits are more accurate in the quantification but have a lower dynamic range as the Plexor HY. The Plexor HY offers a higher dynamic range due to the amplification of a multi-copy target, but a lower accuracy. This lower accuracy can be attributed to the multicopy target. If less than the full set of 20 copies on a genome amplifies, because of for example instability in the target copy number, than the ratio between the amplification between autosomal and gonosomal (Y) target may vary. The dynamic range of the Plexor HY kit is slightly better than that of the other kit (LaSalle et al., Forensic Science International: Genetics, "Analysis of Single and Multi-copy Methods for DNA Quantification by Real-Time Polymerase Chain Reaction"). In a statistical comparison LaSalle et al. demonstrated a significant difference between the two kits.

Another important parameter in forensics is the degradation grade of the DNA that has to be analyzed. Since the amplicon size of the Quantifier Human and PlexoHY vary from 62 to 133 base pairs (bp), significant differences might be expected when the kits are applied to degraded DNA.

SUMMARY OF THE INVENTION

The present invention solves the above identified problem and provides for the following solution as outlined below.

The invention in one aspect relates to a method for quantifying and/or detecting one or more nucleic acids of a genome in a sample, wherein
  a. the nucleic acid is amplified and the locus that is amplified is a multi copy locus within the genome,
  b. the multicopy locus has copies on at least 2 different chromosomes
  c. and the amplification product is detected and/or quantified.

A substantial benefit of this new method is its higher sensitivity and higher stability of the detected target compared to previous methods. Other previously known targets may vary from individual to individual as repetitive elements tend to vary in number (Pavelitz et al., Human U2 snRNA Genes Exhibit a Persistently Open Transcriptional State and Promoter Disassembly at Metaphase, Molecular and Cellular Biology, 20081, p. 3573-3588; Liao et al., Concerted evolution of the tandemly repeated genes encoding human U2 snRNA (the RNU2 locus) involves rapid intrachromosomal homogenization and rare interchromosomal gene conversion, The EMBO Journal, Vol. 16, No. 3, pp. 588, 598, 1997; Jasinska et al., Repetitive sequences that shape the human transcriptome, FEBS Letters 567 (2004) 136-141).

Ideally the locus is not a repetitive element such as a short tandem repeat or per se an element with the following formula: $(A_w C_x G_y T_z)_{2-1000}$ wherein w, x, y, and z can vary from 0 to 10 and represent the number of nucleotides present in the unit. The unit may be repeated from 2 to 1000 times. Another repetitive element is satellite DNA usually within the telomers. Repetitive elements that are also not suited are short interspersed nuclear elements (SINE) and long interspersed nuclear elements (LINE).

Further, the invention relates to the use of a multi copy locus within the genome, wherein the multicopy locus is not a repetitive element and has copies on at least 2 different chromosomes for detecting and/or quantifying the nucleic acids of said genome.

Also, the invention relates to a kit for detecting and/or quantifying human nucleic acids, wherein the kit comprises primer that, under stringent conditions, bind a sequence that shares at least 80% sequence identity to a sequence according to SEQ ID NO. 1 or 52 over a stretch of 80 base pairs.

The following abbreviations are used herein (1) HDA (helicase dependent amplification), (2) PAGE (polyacrylamide gel-electrophoresis), (3) gDNA (genomic DNA), (4) FAM (6-carboxyfluorescein), (5) SNP (single nucleotide polymorphism), (6) NTC (no template control), (7) BHQ (black hole quencher), (8) qPCR (quantitative PCR), (9) HEX (6-carboxy-4,7,2',4',5',7'-hexachlorofluorescein).

DETAILED DESCRIPTION OF THE INVENTION

Method for quantifying and/or detecting one or more nucleic acids of a genome in a sample, wherein
a. the nucleic acid is amplified and the locus that is amplified is a multi copy locus within the genome,
b. the multicopy locus has copies on at least two different chromosomes
c. and the amplification product is detected and/or quantified.

Astonishingly, the inventors have found that multi copy loci that are not a repetitive element are superior to other loci when used for detection and/or quantification of nucleic acids. It is well known, that repetitive elements may vary in copy number between individuals. Accordingly, the present invention relates preferably to the herein cited methods, wherein the multicopy locus is not a repetitive element.

In general, these nucleic acids may have any origin, prokaryotic, eukaryotic or the like. Preferably they are mammalian and more preferably human. This is because one great advantage of the present invention is its application in the field of forensics.

One such sequence is identified in SEQ ID NO. 1 another in SEQ ID NO. 52. SEQ ID NO. 1 is in fact a portion of SEQ ID NO. 52. The inventors have astonishingly found that this sequence and/or sequences that share sequence similarity with it may be found many times in the human genome. Hence, ideally primers and/or probes are used that bind these sequences.

```
SEQ ID NO. 52      TCAACAGGCCACCGTGAGGGAGGAGCTGGGCCGCACGCGGGCTGCTGGGAGGCAGGC
(the underlined    AGGGACTTGGCCCCGAGAGGCCGCCGTGGGGGCAAGAGCTGGGCCTGGAGAGGCCCC
part is SEQ ID     TGGGAGGCAAGGGCGGGGCCTGCAGAGGCTGTTCTCCAACCAGTGCTAGAACTGTAC
NO. 1)             AGGCCACCAGGAGGCAGGAGGTGGGCCCTCAGAGCTTGGCTGGAGAAAGTTCGGGGC
                   CTACAAAGGCGGTTGGGAGCTGGGCAGGAGTTGAGCCAAAAGAGCTTGCTTACTTGC
                   TGGGAGGCAGGGCCGGGAGAGCCCGACTTCAGGACAACTTGGGCCTGCGGCAGTCGC
                   CGGGAGGCCCAACCTTGGCGTGGAGGAGCCCACCGACCGGAGACCATTTGGGGCCTG
                   GAGATGCCATCGGAGGGCAGGAGCTCATCCTGGAGAGGCCACCGTGAGGCCTGACCT
                   GGGCCTGGGGAGCTTGGCTTGAGGAAGCTGTGGGCCGACCAAGGCCGCCAGGAGATG
                   GGTAGGCACTGAGTCCAAAGAGGTTGTTGAGAGGCAGGAATCGGGCCTGGAGACCCA
                   ACCAGGAAGAAGAGCTGGGCCCGGAGAGAATGCACGGAGGGTGCAAGTGGGTCTGGA
                   GAGGCCGACTTGAGGAGGTTCTGGGCCCGGAGAGGCCGCCGGAAGGGAAAAACTGGG
                   CCTGGAAAGGCCGTTGTCAGGAATGAGCCCCATGGGCCTGAAGAGGCCACTGGCAGG
                   CGGGAGCTGGGCCTGCCGAAGCGGCCGAGAGGCAGGAGCTTTGGACTCGGGAGGCCG
                   CAGTGAAGCAACAGCTAGCTGGGCGTGGAGAGTCCGCTGTGAGGCAGAGGCTGGGCC
                   TGTGCAGGCCTTCGGGAGGCAGGAGGCTGGGCCTTGTCGAGGCCTGCAGAGGCCACC
                   GAAAGTCAAAAGCGGGGCTTGGGAAGGCCGCCGGGAGGCATGAGCTGGGCTGGGCCG
                   AAAGAGGCCACTGGGAGGCAGGAGGAGCTGGGCCTGGAGAGGCTGCCAAAAGGCAGG
                   AGCTTCGCCTGAGGATGCCACAGTGAGACACCATCTGGGTCTGGAGGGTCCACTGTG
                   AGGCAGAGGCTGACCTGTAGAGTCCGACAGTAGACAGAAGTTGGGCAAAAGCCTGAT
                   TTGAGGAAGTTTTGGGCTTCAAGAGTCAGCCACGAGGCAGGCACTAGGCCTGGAAAT
                   GGCCTCACAGTCATGAGTTGGGCCTAAATGGGCCACTGTGAGGGAGGAGCTGTGCCT
                   GTTGAGGCTGCTGGCAGGCAGGCAGAAATTTGCCTGGGGCAGCTGCCATGAGGCAA
                   GAGCTGGGCCTGGAAAAAGCCCCTGGGAGGCAAGAGCAGGGCCTGCAGAGGCTGTTC
                   TCAAGTCAAAGCTGGGCCTGTTGATGCCACCGGGAAGCAGAAGGTGGGCCTGGAGAG
                   TTTGACTTGAGGAAGTTTTGGGCCTACATTGGCCGCCATGAGCTGGACAGGAACTGG
                   GCCAAAAAAGGCTGTTGTGAGGCAGCAGTTGTGCCTGTAGACCCAGCCAAGAGGAAG
                   AGGTGGGTCTGGAGAAGCCCCCATGAGGCAGAGGTTGGGCCTGTAGACGCTGACAGG
                   AGGCAGGAGCTGGGCCTGGACAGGTCAACTTGAGGAGATTTTGGGCCTTCATAGGCC
                   ACCAGGAGGCAGTAGTTGGGACTAGAGAGTCTGACTTGAGTAAGTTTTGGGCCCGGA
                   GATGACGTCCTGGGACAGGAGTTGGGCGTGGAGAGGCCACCGTGAGGCATAAGCTGG
                   ATGTAGAGAGGCCAGTGTGAGGCAAGACCTGGGCCTGTCTAGGCTGCTGGGAGACAG
                   GCAGGAATCTGGCCAGGGAAGGTTGCCATGAGACAAAAGTTGGGCCTGGAAAGGCCC
                   TTGTGAAGCATGAGCTTGGCCTAAAGAGGCCACTGGGTGGCAGGAGCTGGGTGTGTA
                   GAAGCTGCTGAAAGGTTGGGAGCTTGGCTTGGGGGGTCCACAGTGAGGTAGATGCTG
                   GGCGT
                   GAAGAATCTGCTGTGAGGCAGACGTTGGGACTGTAGAGGCTGACGGGAGGCAGAGGC
                   TGGGCCTGGAGGGGCCACCAAGATGCAGGAGCTGGGCCTGGAGAGGCTGCAAAGAAG
                   CATGACCTGGGCCTGGTGAGGTCGACTTGAGAAAGTTCAGGGCCTGGAGAGAAGGCT
                   GGGAGGCAGGAGCTGGGTCTAAAGAGGCCATTGTAACGATGGAGCTGTGCCTGTGGA
                   GGCTGTTGTGAGGCAGTAGCCTCATCTGTGGAGGCTGCCGTGACGTAGGGTATGGGC
                   CTAAATAGGCCATTGTGAGTCATGATCTTGGTCTGTAGAGGCTGACTGGAGAAAGTT
                   CTGGGCCTGGAGAGGCTGCCGGGAGGTAGGAGCTGGGCCAAAAGATGTAAGCACATT
                   TGCATTTATTAGGCACTTTATTTCCATTATTACACTGTAATATATAATAAAATAATC
                   ATAGAACTCACCATAATGTAGAATCAGTGGGCGTGTTAAGCTTGTTTTCCTGCAACT
                   GGATGGTCCCACCTGAGCGTGATGGGAGAAAGTAACAGATCAATAGGTATTAGATTC
                   TCATAAGGACGGCGCAACCTTGATCCCTCACATGCACGGTTCACAACAGGGTGCGTT
                   CTCCTATGAGAATCTAACGCTGCTGCTCATCTGAGAAGGTGGAGCTCAGGCGGGAAT
                   GTGAGCAAAGGGGAGTGGCTGTAAATACAGACGAAGCTTCCCTCACTCCCTCACTCG
                   ACACCGCTCACCTCCTGCTGTGTGGCTCCTTGCGGCTCCATGGCTCAGGGGTTGGGG
                   ACCCCTGCTCAAGTGCATCCAAAGCGACCCTTCCCACACCAGTCTTCACAGTGGTCA
                   AGGGCAGCAACCACTTAGCTCCCAAGGCATGTGCCTCAGCTGGCATTTCGTCACAAT
                   CAACAGTAAGTGGTAGCTTGAGTCACTGTGAGGTCACCTACTGGAAATCACCAGCAT
                   CCCATTTCCCACTGGCAAAGAGCTCAGCGCTGCCCCCTGGGAAACCAAACCTATGCC
                   CAAATCCCATCTGTGTGGGTGTATCTCCTGGGACCCTTCCTAACATATTAGTCAGAG
                   TCCAATCAGGAAGCATAAACCACTCAAAAGTTTAAAGTGGTAAAATTTAATACAGAG
                   AATTATTCATTATAACAGGTGAACAGCATAATGAGAGATTGGCTAGCACAAAGTAAA
                   GAGAACTCTAGAGAATATAGGACTAGCCCAGGCCAGGCATGGTGGCTCAGGCCTGAA
                   ATTCCAGCAATTTGAGAAGCTAATGCAGGAGGATTGCTTAAGGCCAGGAGCTAGAGA
                   CCGGTCTGGACAACAGAGTGAGACCCTGTCTCTATCCAAAAGAAGAAAAAAGTTAGC
```

```
                         -continued
TGGTGGTGGTAGTGCACACTTGCAGTCCCAGCTACTCGGAATGCGGAAGTTTGAGCC
TGGGAGGTCAAGGCTGCAGTGAGGCATGATTATGCCACTACAGTCCAGCCTGGTGAC
AGAGCAAGACCCTGTCTCAAAGAACAAAACAACAACAACCATTTACAGACAGAAAAG
AAATAGAGCTAATAAGCTGAGGAAAGATGTTGAAATGTGACAAGTAAAGTAACATGA
GGTCTTTTGTCTATTTAAAATAATCAAACAAAAAATGACTTACTAAATTATAATACC
CTGTGCTGGCAAAGGTGCAGTGAAATGGGCACTTTCTTATACTATGAGAGGTGGTTA
AATTGTGTATAAGCCTTCCCGGGTAAAGCCTGTCAATTTTTTAAAATAATGGAGACA
GGGTCTCACCATACTGCCATACTGCCTCCTCCAACTCTTGGCCTCAAGCAATCCTCC
TCTCTTAGCCTCCCAAAGTGCTAAGATTATAGCTGGGAGGCACCCAAAACCCTGTCA
ATTTACATCAAGGGTAAGGAGAATGTCCATTCACCATGACTCACAGTAATCTTACTT
CTGGGGAGACAATTCAGTCTAAACAAAAGGTCATCTGTACACACACAGTAAAAATCT
GGGAGTAACTGAAGACAGAGTTGGTAAGTGAAATAAGAAACAGTTATAAGAAATTAA
ACTATGGTATCAATAGGCACCTGGTACAAAAGGTCAGTTGATGTTGGCTGCTACTTT
TTTGTTGTTTTGAGACAGGGTCTCACTCTGTCACCCAGGCTGGAGTGCAGAGGCCTG
ATCATGACTCACTGCAGTCTCAGCCTCCCTGGGCTCAAGTGATCCTCCCACCTCAGC
CTCCCAAGTAGCTGGGACTACAGGAACATGCCACCACACTAGGCTAATTCATGTATT
TTTCTGTAGGGATGGTGACTCCCCCTTTGTTTCCAAGGCCTATCGCAAACTCTTGGC
CTCGAGCCATCCTCCTGCCTCAGCCTCCCAAAGTGTTGCGATTACCAGTGTGAGCCA
CCACACCTGGCCAGCTGCTACTTTTATCAATATTATTCTTATTCCACTCAATTAAAA
ATTATTATTTTCAAGGCTATGCAACAGTATGTATCCTACAGCGTAATTGTAAAAACA
TATACAGTCGTCGTCCCTCAGTATACAGAATTAGTTCCAGCCCCCCATCTCTGCATA
TACCAAAATCCATGCTTACTCACGTTTCGCTGTCACCCCTCTGGAATCCACGTATAC
GAAAATTCCAAATATTAGTTGGGCATAGTGGCAAGCACCTGTAGTCTCAGCCACGTG
GGAGGTTGAGGTGGGAGGATCGCTTCAGCCTGGAAGGTTGAGGCTGCAGTCAGCTGC
GATAGCACTACTACACTCCAGCCTTGGACAACAGAGGGAGACCCTGTCTCAGAACAA
AAAAAAATAAAAAATAAAAAATAAAACAGGTTAGAAACTGTGATGAGGTCTGCTGGG
CAAAATTCCATATAAGCAAAGTATAAATTAATAAAGCAAATCGTGATAAATTAGTAC
GATTGACTTTCTGGAGTTTCTGACAATAAAAGTAAGGAAAATGCAGAACACAAAGAC
AGAGAGTAAAAAGAGAAATTAGGAAAGCATTCTACATGTTGAATAGGAAGACACTGG
CCATGTTCGTGCAGCGGCAGTATGTCGTGACATGACATACCTTGGAGAGAAGTTAAC
AGATGAGGAAGTTGATAAAAATCATCAGAGAAGCAAAATACTGGTAGGGACACTCAA
GTAAACCATGAAATTTCCATAACTTATGTCAGCAAAGTGGGAATATTGTACAGTGTG
TGTTGAAGTTCCTATACAACATTGTTTATCTGCCTTTTGTTTGTTGTAAGGAATGT
ACATACTAAAAGTTCTTCTTGCTGTCAAAAGAATATGTGTGAATAAGTCATTTTAAC
TTATTCTTCTGTTTTTCTTTTATCTTCCTGCCATCATCCCACAGCCTTACTTTAGAA
ATTTTTTTTTTAGAAAATTGAACAAGTGCTCCTTGTGGTGGCACATGCCTCGAGGAT
GGGAGGCAGGGGTGGAAGGGTCACTTGAGGCCATTAGTTTGACACCAGCCTGGCCAA
CAAAGTGAGACCCCGTGTCTACAAAACAATTTAAAAATTAGCCAAGTATCATCATGT
ATACCTACAGTCCCAGCTA
```

The sequences distributed throughout the genome are not all exactly identical. It is important that the selected primers bind also to the nearly identical sequences. Thus, ideally the locus shares at least 60%, 70%, 80%, 90% or even 95% or 98% sequence identity to a sequence according to SEQ ID NO. 1 or SEQ ID NO. 52 over a stretch of 80 base pairs.

The determination of percent identity between two sequences is accomplished using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program, score=100, word length=12, to obtain percent identity between nucleotide sequences. BLAST protein searches are performed with the BLASTP program, score=50, word length=3, to obtain percent identity between amino acid sequences. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

It is an aspect of the invention that multiple copies are amplified. Ideally, at least 4, 5, 6, 7, 8, 9, 10, 11, 12, 13, 14, 15, 16, 17, 18, 19, 20, 21, 22, 23, 24, 25, 26, 27, 28, 29 copies on various chromosomes are amplified. SEQ ID NO. 1, 52 or sequences very similar thereto are present up to 29 times in the human genome. This is not just astonishing but provides for the power of the present method. Also, the copies may be found on various chromosomes such as 1, 4, 5, 7, 11, 16.

The amplification method is either a non-isothermal method or an isothermal method.

The non-isothermal amplification method may be selected from the group of polymerase chain reaction (PCR) (Saiki et al. (1985) Science 230:1350), quantitative real-time PCR (rt-PCR), ligase chain reaction (LCR) (Landegren et al. (1988) Science 241:1077-1080). Polymerase chain reaction amplification is preferred.

The isothermal amplification method may be selected from the group of helicase-dependent amplification (HDA) (Vincent et al. (2004) EMBO rep 5(8):795-800), thermostable HDA (tHDA) (An et al. (2005) J Biol Chem 280(32):28952-28958), strand displacement amplification (SDA) (Walker et al. (1992) Nucleic Acids Res 20(7):1691-6), multiple displacement amplification (MDA) (Dean et al. (2002) Proc Natl Acad Sci USA 99(8): 5261-5266), rolling-circle amplification (RCA) (Liu et al. (1996) J Am Chem Soc 118:1587-1594), restriction aided RCA (Wang et al. (2004) Genome Res 14:2357-2366), single primer isothermal amplification (SPIA) (Daffom et al. (2004) Biotechniques 37(5):854-7), transcription mediated amplification (TMA) (Vuorinen et al. (1995) J Clin Microbiol 33: 1856-1859), nicking enzyme amplification reaction (NEAR) (Maples et al. US2009017453), exponential amplification reaction (EXPAR) (Van Ness et al. (2003) Proc Natl Acad Sci USA 100 (8):4504-4509), loop mediated isothermal amplification (LAMP) (Notomi et al. (2000) Nucleic Acids Res 28(12): e63), recombinase polymerase amplification (RPA) (Piepenburg et al. (2006) PloS Biol 4(7):1115-1120), nucleic acid sequence based amplification (NASBA) (Kievits et al. (1991) J Virol Methods 35:273-286), smart-amplification process (SMAP) (Mitani et al. (2007) Nat Methods 4(3):257-62).

By "isothermal amplification reaction" in context of the present invention it is meant that the temperature does not significantly change during the reaction. In a preferred embodiment the temperature of the isothermal amplification reaction does not deviate by more than 10° C., preferably by not more than 5° C., even more preferably not more than 2° C. during the main enzymatic reaction step where amplification takes place.

Depending on the method of isothermal amplification of nucleic acids different enzymes are required for the amplification reaction. Known isothermal methods for amplification of nucleic acids are the above mentioned, wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and/or nucleases.

"Helicases" are known by those skilled in the art. They are proteins that move directionally along a nucleic acid phosphodiester backbone, separating two annealed nucleic acid strands (e.g. DNA, RNA, or RNA-DNA hybrid) using energy derived from hydrolysis of NTPs or dNTPs. Based on the presence of defined helicase motifs, it is possible to attribute a helicase activity to a given protein. The skilled artisan is able to select suited enzymes with helicase activity for the use in a method according to the present invention. In a preferred embodiment the helicase is selected from the group comprising helicases from different families: superfamily I helicases (e.g. dda, perA, F-plasmid traI protein helicase, uvrD), superfamily II helicases (e.g. recQ, NS3-helicase), superfamily III helicases (e.g. AAV rep Helicase), helicases from DnaB-like superfamily (e.g. T7 phage helicase) or helicases from Rho-like superfamily.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescence label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

Ideally, when detecting nucleic acids helicase-dependent amplification (HDA) is used. And, when quantifying nucleic acids real-time PCR (rtPCR) is used.

Ideally, the amplification product size is between 80 bp and 200 bp. The amplification product may also be longer, i.e. 300 bp, 400 bp or even longer.

The primers ideally used for amplification have a nucleotide sequence that differs from SEQ ID NO. 2, 3, 5, 6, 8, 9, 10, 11 and 12 by no more than 5 nucleotides over a stretch of 18 nucleotides.

Oligonucleotide primers may be prepared using any suitable method, such as, for example, the phosphotriester and phosphodiester methods or automated embodiments thereof. In one such automated embodiment diethyl phosphoramidites are used as starting materials and may be synthesized as described by Beaucage et al. (1981) Tetrahedron Letters 22:1859-1862. One method for synthesizing oligonucleotides on a modified solid support is described in U.S. Pat. No. 4,458,006. It is also possible to use a primer, which has been isolated from a biological source (such as a restriction endonuclease digest). Preferred primers have a length of about 6-100 bases, more preferably about 20-50, most preferably about 20-40 bases.

DNA Quantification Using Real-Time PCR

During PCR, the amount of DNA theoretically doubles with every cycle. After each cycle, the amount of DNA is twice what it was before.

The absolute amount of DNA in an unknown sample is preferably determined using external standards. The standard is usually very similar to the unknown sample; the primer binding sites of the standards should be identical to those in the target sequence. This ensures that the target in both the standard and in the unknown sample is amplified with equivalent efficiencies, which is essential for quantification.

Using real-time PCR techniques, fluorescence is detected and measured in the real-time PCR thermocycler, and its geometric increase corresponding to exponential increase of the product is used to determine the threshold cycle (CT) in each reaction.

The unknown and each of the standards are amplified in separate tubes. A standard curve (plot of CT value/crossing point against log of amount of standard) is generated using different dilutions of the standard. The CT value of the unknown samples is compared with the standard curve, allowing calculation of the initial amount of the target. It is important to select an appropriate standard for the type of nucleic acid to be quantified. To generate a standard curve, at least 5 different amounts of the standard should be quantified, and the amount of unknown target should fall within the range of the standard curve. Hence, in one embodiment also the above quantification steps are performed.

The invention also relates to the use of a multi copy locus within the genome, wherein the multicopy locus ideally is not a repetitive element for detecting and/or quantifying the nucleic acids of said genome. In one embodiment, the use of said multi copy locus is intended for detecting and/or quantifying nucleic acids according to the herein cited methods or for analyzing the status of degradation of human DNA.

Forensic scientists often deal with case-work samples from different sources. These samples can be degraded due to different factors such as environmental stress.

The invention also relates to a human DNA degradation marker system with higher sensitivity and accuracy than state of the art methods.

From the literature it is known that the integrity of DNA can be assessed by targeting at least two different genomic regions through qPCR in the same reaction vessel. These two co-amplified targets have to differ in their length, but the amplification efficiencies using non-degraded DNA need to be equal. Hence, if the DNA is not degraded, both the shorter and the longer PCR system will be amplified with the same efficiency. If the analyzed DNA is compromised, the mean length of the DNA fragments present in the sample will drop which leads to a decrease of the amplification efficiency. Since the template DNA of the longer system is statistically more compromised than the template of the shorter one, the amplification efficiency of the longer PCR system will be lower compared to the shorter one. With decreasing average fragment length in the sample, the gap of amplification efficiencies between both PCR systems will increase. Consequently, the ratio of the quantification of both PCR systems gives the information about the degradation state of the DNA to be analyzed.

An example is shown in the FIG. 8 below. The longer PCR system is addressed using the "scorpion probe and primer degradation" (SEQ ID NO. 53 and 54) in the Crimson channel of the Rotor-Gene Q, yielding a PCR product of 363 bp. The shorter PCR system is addressed in the Green Channel of the same instrument using the primer and scorpion outlined above yielding a PCR product of 146 bp. The quantification of non-compromised in comparison to degraded DNA samples (on a mean fragment length of about 500, 300 and 150 bp) is shown. The quantification using both PCR systems is given in the FIG. 9. The ratio of both quantifications is a possible solution to express the degradation state of the DNA to be analyzed. A higher ratio indicates a higher degree of degradation of the analyzed DNA; see also FIG. 9.

Preferably, the locus shares at least 80% sequence identity to a sequence according to SEQ ID NO. 1 or 52 over a stretch of 80 base pairs. Sequence identity may be determined as outlined above.

The invention also relates to a kit for detecting and/or quantifying human nucleic acids, wherein the kit comprises primer that under stringent conditions bind a sequence that shares at least 80% sequence identity to a sequence according to SEQ ID NO. 1 or 52 over a stretch of 50 base pairs. Binding conditions are known to those skilled in the art and can be found in Current Protocols in Molecular Biology, John Wiley & Sons, N.Y., 6.3.1-6.3.6, 1991. Stringent conditions can be defined as equivalent to hybridization in 6× sodium chloride/sodium citrate (SSC) at 45° C., followed by a wash in 0.2× SSC, 0.1% SDS at 65° C. In a preferred embodiment, the kit is intended for detecting and/or quantifying nucleic acids according to the herein cited methods.

Preferably, at least one primer in the kit has a nucleotide sequence that differs from SEQ ID NO. 2, 3, 5, 6, 8, 9, 10, 11 and 12 by no more than 5 nucleotides over a stretch of 18 nucleotides.

FIGURE CAPTIONS

FIG. 1
A part of the genome region identified is shown.

Figure 2:
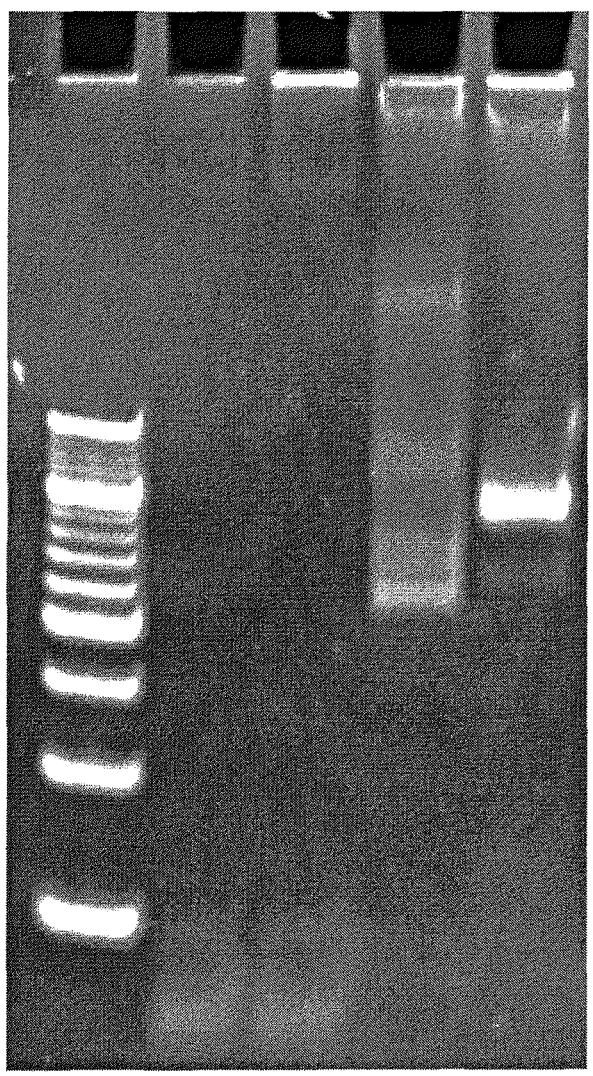

FIG. 2
Result of the PAGE analysis of a HDA reaction. Lane 1: O-RangeRuler 10 bp DNA Ladder (Fermentas); Lane 2 and 3: HDA reaction with other primers; Lane 4: HDA with primers hT-For2 and hT-Rev2 without gDNA; Lane 5: HDA with primers hT-For2 and hT-Rev2 with 10,000 cp human gDNA.

Figure 3:
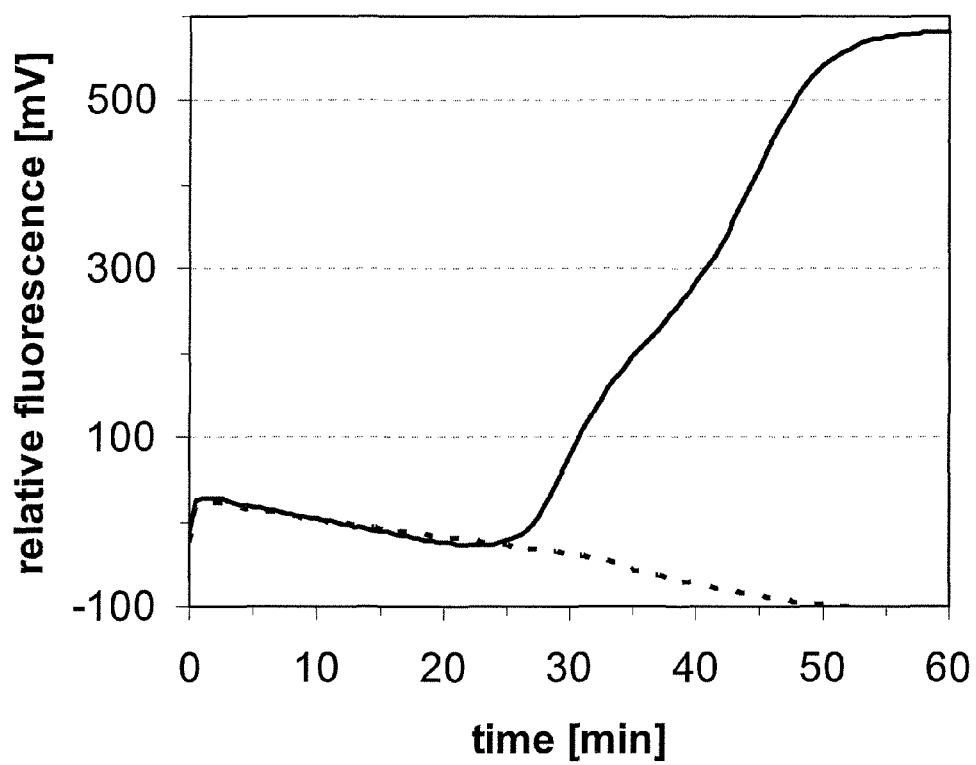

FIG. 3
FIG. 3 shows the result of real-time HDA reactions. Dotted line: control reaction without human DNA; solid line: reaction with 10,000 copies human gDNA.

Figure 4:
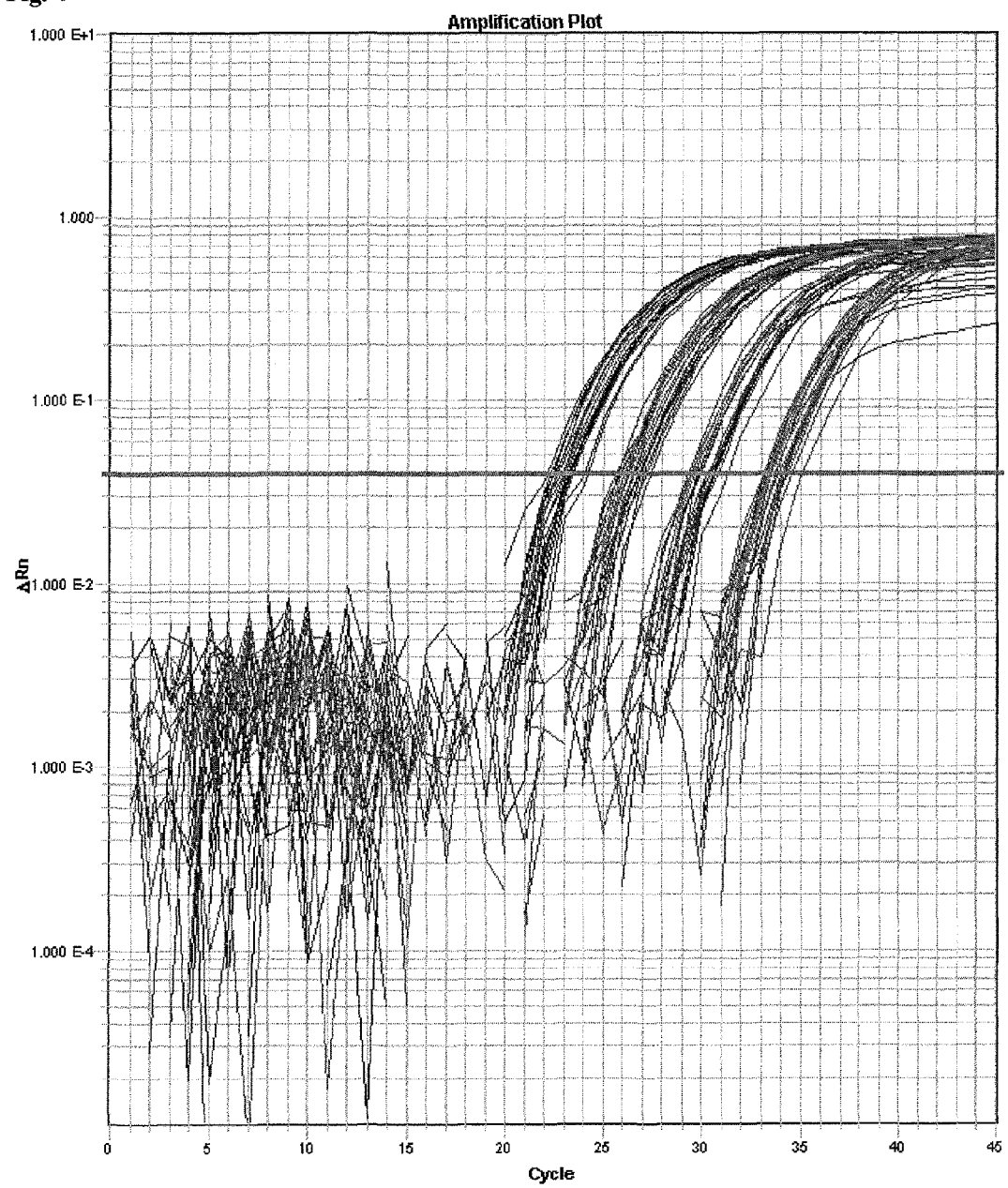

FIG. 4
qPCR data is shown from a dilution series (10 ng-10 pg human gDNA).

Figure 5:
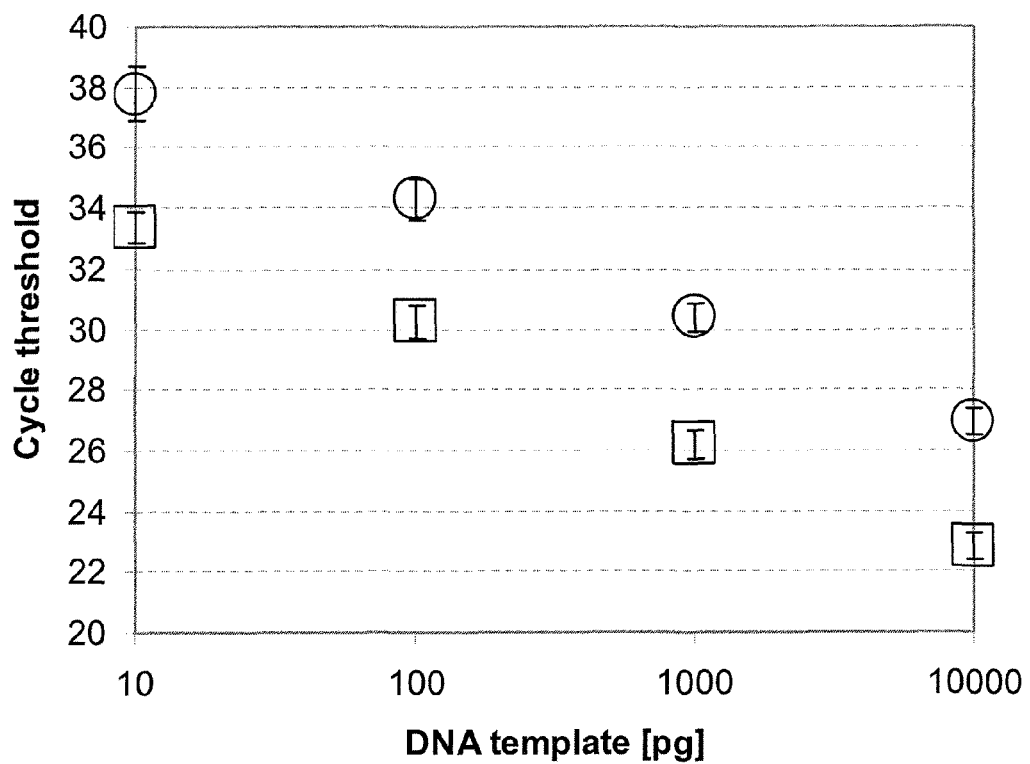

FIG. 5
Diagram of Ct-values of the multicopy assay (squares) and single copy assay (circles); Template DNA was added at 10 pg to 10 ng gDNA per reaction.

FIG. 6
Overview of sequences. SEQ ID NO. 2 and 3 are primers that amplify the first underlined portion of SEQ ID NO. 1. SEQ ID NO. 11 and 12 are scorpion primers that amplify the second underlined portion of SEQ ID NO. 1

FIG. 7
FIG. 7 shows the regions amplified by primer pairs 11 and 12, 5 and 6 and 8 and 9.

Figure 8:
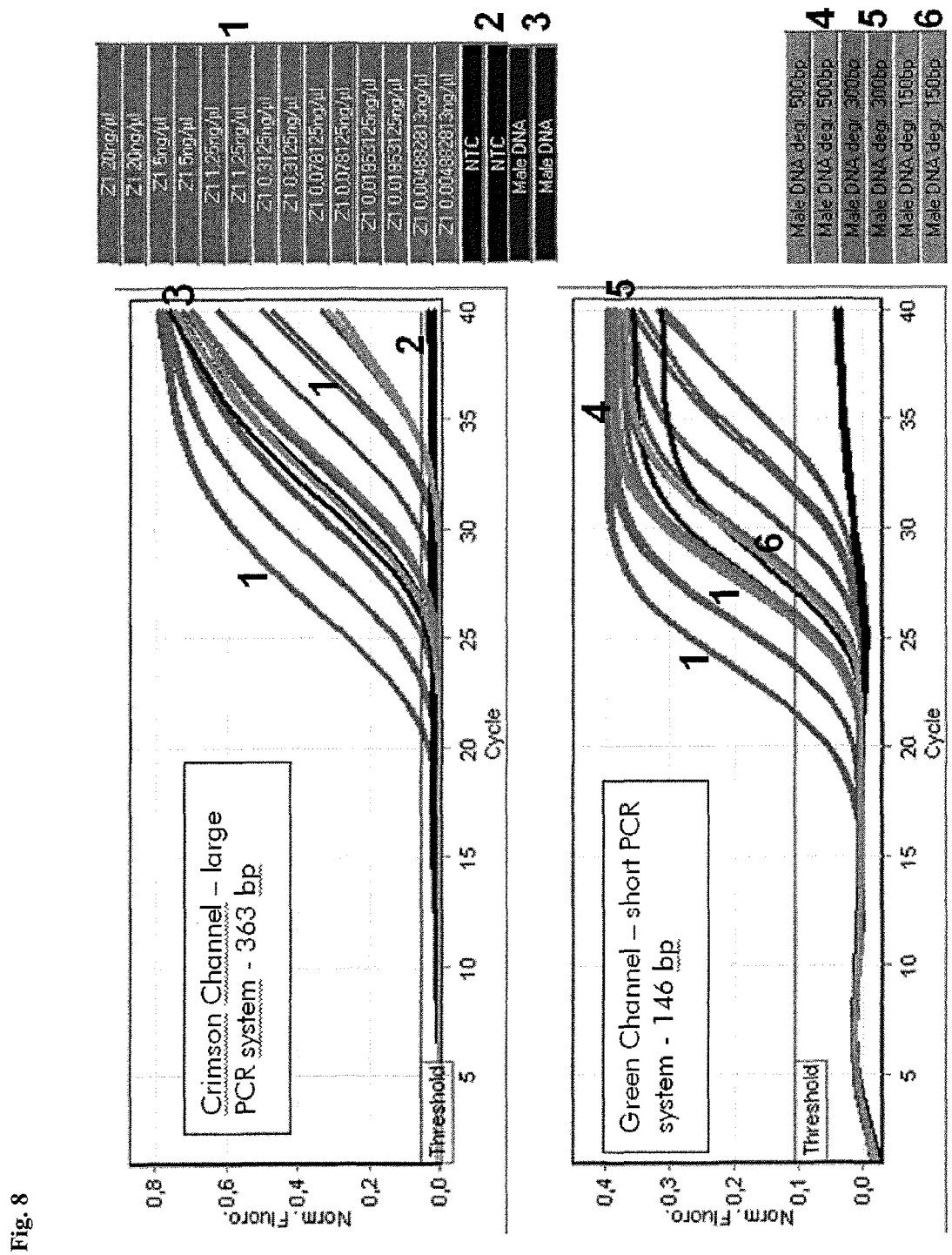

FIG. 8
FIG. 8 shows the measurement of degraded DNA in humans.

FIG. 9
FIG. 9 shows the measurement results of degraded DNA in humans.

Figure 10:
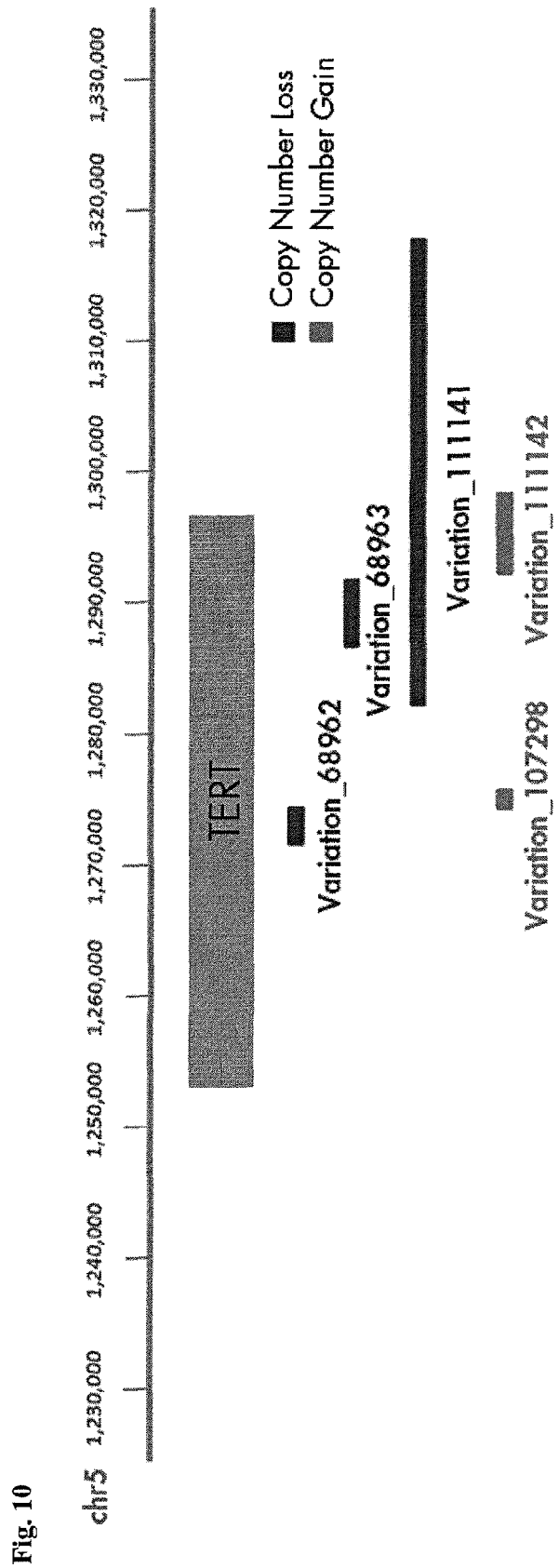

FIG. 10
FIG. 10 shows the measurement results of variable copy number.

Figure 11:
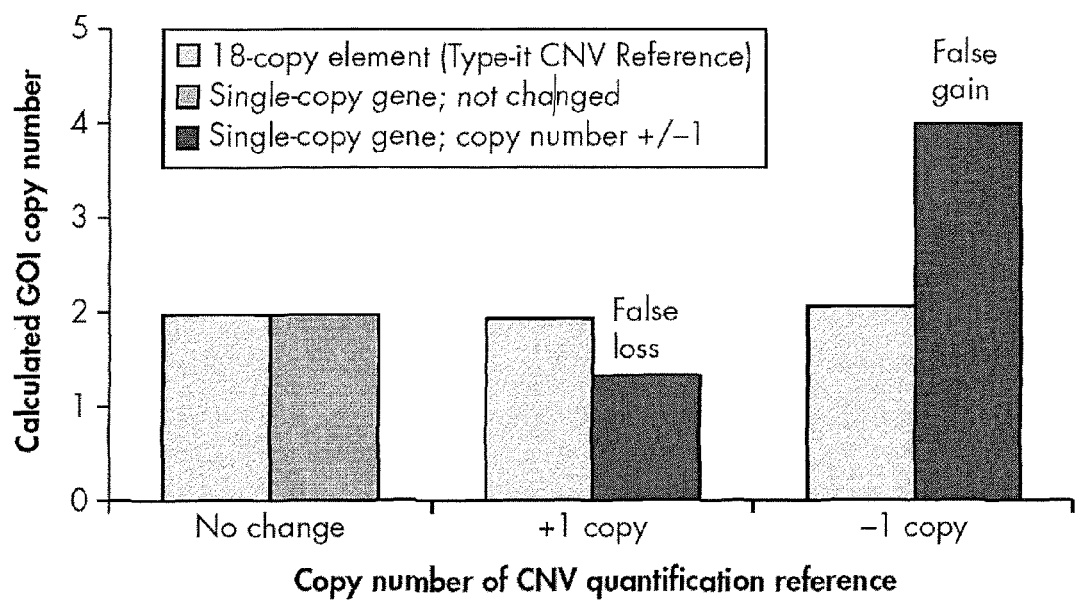

FIGS. 11A and B
FIG. 11 shows the measurement results of variable copy number.

Figure 12:
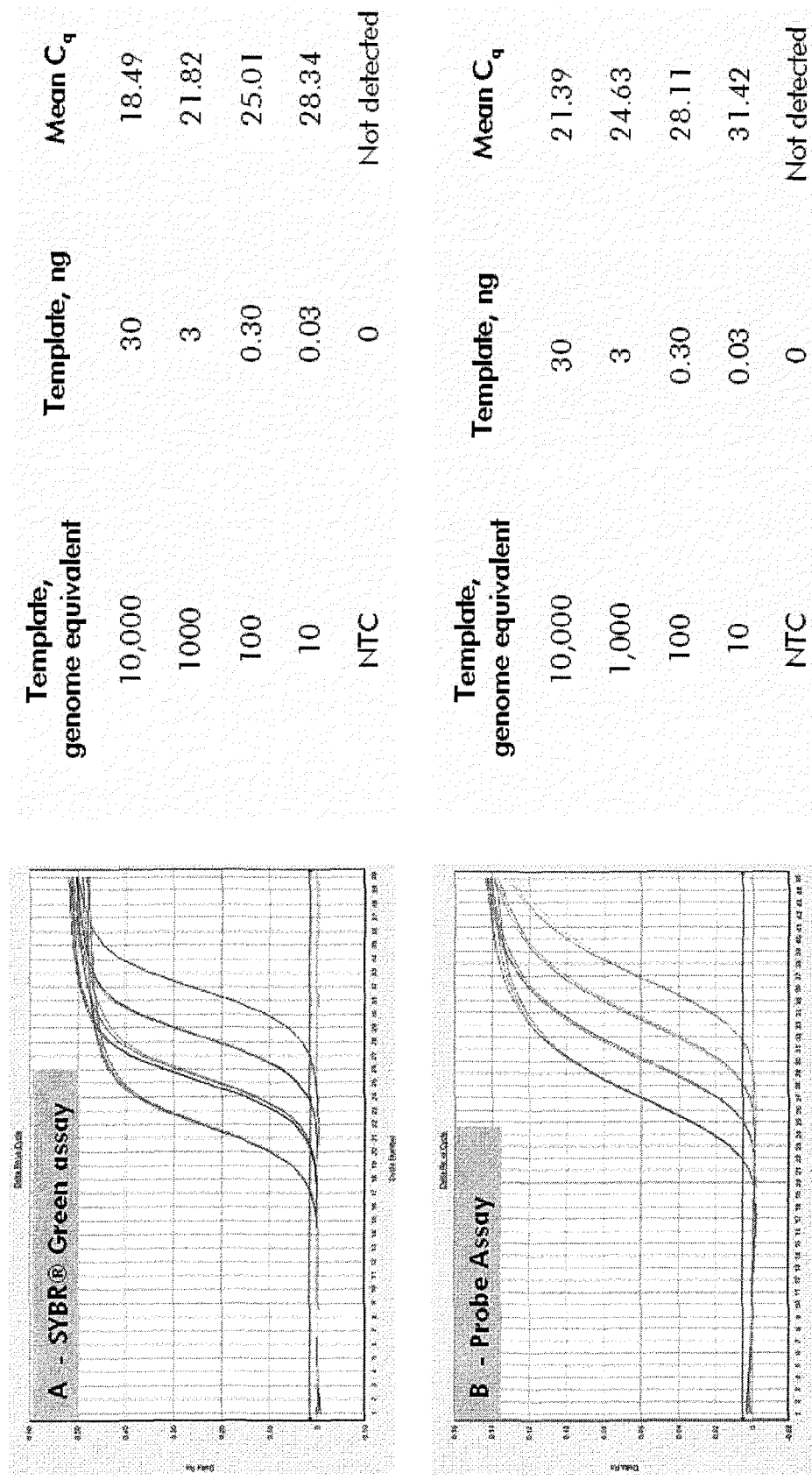

FIG. 12
FIG. 12 shows the measurement results of variable copy number.

EXAMPLES

The great advantage of the invention is that primer and probes may be created that allow for a DNA quantification and/or detection that work regardless of sex, ethnic or regional background. This provides for a great advantage over existing technologies.

The amplification of human DNA is relevant for various areas of molecular diagnostics as well as forensics. In forensic methods DNA typing is performed by amplifying certain regions of DNA. These are often called short tandem repeat regions. In order to obtain proper results it is essential to apply the template DNA with a certain, narrow concentration range. A further area where it is important to know the exact amount of DNA that is added to the reaction is HLA typing as well as single nucleotide polymorphism (SNP) analysis. HLA typing is performed in order to analyze whether or not a transplant will be rejected. SNP analysis is often used in order to analyze the genetic background of a person, e.g. to assess for hereditary diseases as well as to analyze whether a person is predisposed to certain types of cancer.

Further, in some existing methods, which are similar to the present method, multiple copies of the locus to be amplified lie on one chromosome in a tandemly repeated motif and there are different variants in the population, which lead to differing results. Although this is not proven, it seems to be one way to explain the drawbacks of the existing tests. A common amplification method also outlined above is the HDA method. U.S. Pat. No. 7,662,594 displays in FIG. 6 an amplification result achieved when using too much DNA. Hence, it is apparent that in some amplification methods the exact amount of DNA to be added to the reaction needs to be known and is essential for the success of said reaction. The advantage of the present method lies in the fact that a genomic region was identified initially by searching literature, which turned out to be useless and later, by searching data bases, which was also not very helpful, that provides for reproducible amplification from multiple copies, in particular from different chromosomes, wherein no locus lies on one of the X or Y chromosomes. Starting from the general transcription factor II H subunit 2 gene (GTF2H2) the inventors identified a further sequence, which is, however, not part of this gene. The identified DNA region is approximately 2000 bp in size and lies on chromosome 11 (Pos. 69000 bp-71000 bp). The sequence is shown in SEQ ID NO. 1 in FIG. 6.

Further sequences may be found throughout the genome, which share large sequence identity with the sequence identified on chromosome 11.

```
hT-For1
                                        SEQ ID NO. 2
(5'-AGTGGGTCTGGAGAGGCCGACTTG-3')

hT-Rev1
                                        SEQ ID NO. 3
(5'-TCAGGCCCATG GGGCTCATTCCT-3')
```

The primers identified above accomplish an amplification reaction which amplifies 29 loci distributed throughout the human genome (see FIG. 1). Further oligonucleotides were synthesized as primers as well as probes also for isothermal reactions. In order to compare quantitative PCR between multi copy targets as invented herein and single copy targets the following primers and probes were created.

```
hT-For1 and hT-Rev1 and probe hT-Pro1
                                        (SEQ ID NO. 4)
(5'-FAM-TTCTGGGCCCGGAGAGGCCGC-BHQ1-3')
```

The comparison was between the method according to the present invention and a single copy gene quantification with the cmyc gene. In contrast to cmyc 27 loci exist which can be amplified and probed with the oligonucleotides outlined above. The reaction comprised the following components.

1× QuantiTect Multiplex Mastermix (QIAGEN)
400 nM hT-For1 bzw. cmyc-fwd
400 nM hT-Rev1 bzw. cmyc-rev
200 nM hT-Pro1 bzw. cmyc-probe
0 bis 10,000 copies human genomic DNA The reaction was cycled with a Rotor Gene 6000 (QIAGEN) with the following PCR profile, 10 minutes at 95° C. then 40 cycles wherein each cycle consisted of 10 sec at 95° C. and 45 sec at 60° C. The PCR efficiency was the same for both primer systems. The normalized probe fluorescence of the hT-For1/Rev1-PCR reached the given threshold value 4.2±0.2 cycles earlier than the probe fluorescence of the cmyc-PCR reactions. Calculating this back to the template concentrations this calculates to an 18 times higher concentration of DNA amplification template for the hT-For1/Rev1-reaction than for the cmyc reaction. This does not equate to the theoretical ratio of the 27:1, but is very close.

Isothermal amplification was also performed for multi copy locus using the HDA method. A number of different forward and reverse primers were created for the isothermal amplification reactions. The best combination was hT-For2 (5'-GCAGAAGGTGG GCCTGGAGAGTTTGAC-3'; SEQ ID NO. 5) and hT-Rev2 (5'-CCTTTTTTGGCCCAGTTCCT-GTCCAGC-3'; SEQ ID NO. 6). Detection of the reaction products is possible both as end-point measurement as well as real time measurement. The HDA reaction comprised the following components.

20 mM Tris/HCl pH 8.8
40 mM NaCl
10 mM KCl
400 nM dNTP Mix
3 mM dATP
4 mM MgCl$_2$
0.2× EvaGreen
1.75 µl IsoAmp Enzymmix (Biohelix)
100 nM hT-For2
100 nM hT-Rev2
0 to 10,000 copies human genomic DNA This solution was distributed into:
Premix I: 15 µl vol. [hT-For2; hT-Rev2; EvaGreen; human genomic DNA; H$_2$O]
Premix II: 8 µl vol. [Tris/HCl pH 8.8; NaCl; KCl; dNTP Mix; dATP; enzyme mix; H$_2$O]
start sol.: 2 µl 50 mM MgCl$_2$ The reaction was performed as follows:
15 µl premix I were incubated for 2 minutes at 95° C. in a PCR-cycler. Thereafter, the reaction was cooled to 4° C. and then heated again to 65° C. using an ESE Quant Tubescanner (QIAGEN GmbH). After 1 minute 8 µl of premix II were added to the prewarmed premix I and the reactions were mixed. After another 1 minute the HDA reaction was initiated and incubated for 60 minutes at 65° C. After the incubation has finished the results were analyzed using a 12% polyacrylamide gel and this gel was then stained with ethidiumbromide. The result is presented in FIG. 2. Lane 4 shows a very strong DNA band with a size of about 90 bp. This corresponds very well with the calculated amplicon length of 88 bp. The negative control is shown in lane 3. The negative control does not show an amplification product around 90 bp in size. A further experiment was performed that shows that the reaction may also be followed by the additional fluorescently marked oligonucleotide probe hT-Pro2 (5'-FAM-GGAAGTTTTGGGCCTACATTGGCCGCCATG-BHQ1-3') (SEQ ID NO. 7).

FIG. 3 shows the real time HDA reaction, which was performed analogous to the reactions outlined above. The only difference is that 60 nM labelled probe hT-Pro2 was added and the primers were concentrated differently (40 nM hT-For2, 120 nM hT-Rev2). FIG. 3 shows that the HDA reaction using human genomic DNA as amplification template worked well. After about 25 minutes the fluorescence signal raised strongly. This was the result of binding of the probe oligonucleotide hT-Pro2 to the amplified target.

Further experiments were performed as quantitative real time PCR experiments.
The following oligonucleotides were used:

```
hT-For3
                                        (SEQ ID NO. 8)
(5'-AAGGTGGGCCTGGAG AGTTT-3')

hT-Rev3
                                        (SEQ ID NO. 9)
(5'-CCTTTTTTGGCCCAGTTCCTGT-3')

hT-Pro3
                                        (SEQ ID NO. 10)
(5'-HEX-AAG TTTTGGGCCTACATTGGCCGC-BHQ1-3')
```

These primers and probe hybridize to and amplify 14 loci in the human genome.
The template was genomic DNA from EDTA-blood from 5 males and 5 females isolated with the QiaAmp Maxi Kit (Qiagen).
The reaction comprised the following components:
1× QuantiTect Multiplex ROX Mastermix
400 nM hT-For3
400 nM hT-Rev3

200 nM hT-Pro3

10 pg to 10 ng human gDNA per reaction

The PCR profile was as follows: 15 min 95° C. initial incubation followed by 50 cycles wherein each cycle consisted of 1 min at 95° C. and 1 min at 60° C. The PCR amplification fluorescence curves are shown in FIG. 4.

Within the same experiment it was analyzed whether or not the multi copy assay according to the present invention has advantages over the single copy method according to prior art. The fluorescence signals of the hT-For3/hT-Rev3/hT-Probe3 assay (multi copy) in the HEX-channel were compared to the signals of the cmyc assay (single copy) in the FAM-channel. The result is shown in FIG. 5. The fluorescence signals of the multi copy assay crossed the threshold level 4.2±0.2 cycles earlier than the fluorescence signals of the single copy cmyc assay. This calculates to an 18-fold concentration of the multi copy target compared to the single copy target. Hence, the theoretical 14 different binding loci of the multi copy locus assay are well reflected by this experiment.

Further the invention and sequences SEQ ID NO. 1 and 52 may be used to analyse degradation of human DNA in a sample. Preferred probes and primers are as follows for said use.

```
Scorpion probe  5' - Quasar705 - ccgcgttgggagcttggcttggcgcgg-BHQ-2-Spacer
Degradation     18-atctacctcactgtgga 3' (SEQ ID NO. 53)

Primer          5'-AGGAGATTTTGGGCCTTCAT-3' (SEQ ID NO. 54)
Degradation
```

Another surprising application for the multi-copy target is as a reference gene for the Copy Number Variation (CNV) analysis.

Copy number variation (CNV), changes of the DNA copy number in the genome, has been recently shown to be a widespread phenomenon affecting around 10-20% of the human genome. The occurrence of CNVs has been associated with various diseases such as autism, autoimmune disorders, and cancer.

The most commonly used molecular biology tools for discovery of CNVs are microarray analysis and next-generation sequencing (NGS). These two high-throughput methods can discover multiple potential CNVs, which subsequently require validation using an independent method. Once validated, the confirmed CNVs can be examined in a large number of samples to identify a statistically significant association between the CNV and the phenotype.

Quantitative PCR (qPCR), with its ease of use, sensitivity, and scalability, is often the method of choice for CNV validation and association studies. The relative quantification principle is used for this application: a reference gene, whose copy number is presumed to be constant among samples to be compared, must first be defined. The copy number of the gene of interest (GOI) is then calculated based on the Cq difference of GOI and reference gene among different samples.

Since the consistent copy number of the reference gene is essential for the qPCR-based CNV quantification, we compared the reliability of commonly used single-copy reference genes, such as TERT (telomerase reverse transcriptase) with a new method using a multi-copy target. The multi-copy target as reference target offers a more sensitive and reliable CNV quantification results compared with single-copy genes.

A single-copy gene is a less reliable reference for copy number calling. TERT, a single copy gene that is commonly used as reference gene for qPCR-based CNV validation, is subject to copy number variation itself; see FIG. 10.

The figure shows the positions of TERT gene as well as five known CNVs on chromosome 5. Based on information from Database of Genomic Variants.

In addition, there are 517 TERT single nucleotide polymorphisms (SNPs) documented in dbSNP database. A SNP within the CNV reference gene sequences recognized by a qPCR primer or probe can lead to reduced qPCR efficiency and later Cq value and subsequently cause false copy number calling.

More reliable qPCR-based copy number quantification can be achieved by using multi-copy genetic elements, distributed through the entire genome, instead of a single-copy gene as reference gene for ΔΔCq analysis.

The theoretical calculation below illustrates the influence of loss or gain of 1 copy from the CNV reference gene on the Cq values of the reference, as well as the copy number calling of the GOI. Assumptions are: 100% qPCR efficiency for reference and GOI; GOI is a single-copy gene whose copy number in test samples is not changed (NC). CNV quantification reference is either a 18-copy genetic element or a single copy gene; see FIG. 11.

Loss or gain of one copy from the single-copy reference gene will cause false GOI copy number calling. The GOI copy number calling is not affected by loss or gain of one copy from the multi-copy reference.

SybrGreen-based qPCR accurately quantifies GOI and the multi-copy target reference element.

This method relies on the comparison of the Cq value for both the GOI and the multi-copy target run in the same experiment. The primer used for these experiments are SEQ Nr.8 and SEQ Nr. 9.

Probe-based qPCR accurately quantifies GOI and the multi-copy target reference element simultaneously. This method relies on a duplex, probe-based qPCR method that accurately quantifies both the GOI and the multi-copy target in one qPCR reaction.

The primer and the probe used for these experiments are SEQ ID NO.8, SEQ ID NO. 9 and SEQ ID NO.10; see also FIG. 12.

The invention claimed is:

1. A method of quantifying one or more nucleic acids of a genome in a sample comprising:
   a. amplifying a nucleic acid comprising a non-repetitive, multicopy locus, the locus having copies on at least 2 chromosomes and a sequence that shares at least 80% sequence identity over a stretch of 80 base pairs to a nucleic acid sequence of SEQ ID NO.1 or SEQ ID NO.52 to produce an amplification product;
   b. detecting the amplification product; and
   c. quantifying the amplification product.

2. A method of detecting one or more nucleic acids of a genome in a sample comprising:
   a. amplifying a nucleic acid comprising a non-repetitive, multicopy locus, the locus having copies on at least 2 chromosomes and a sequence that shares at least 80% sequence identity over a stretch of 80 base pairs to a nucleic acid sequence of SEQ ID NO.1 or SEQ ID NO.52 to produce an amplification product; and
   b. detecting the amplification product.

3. A method of analyzing the state of possible degradation of human DNA comprising:
   a. amplifying a nucleic acid comprising a non-repetitive, multicopy locus, the locus having copies on at least 2 chromosomes and a sequence that shares at least 80% sequence identity over a stretch of 80 base pairs to a nucleic acid sequence of SEQ ID NO.1 or SEQ ID NO.52 to produce an amplification product;
   b. detecting the amplification product;
   c. quantifying the amplification product; and
   d. determining the state of possible degradation of human DNA in the quantified amplification product.

4. A method of analyzing Copy Number Variation (CNV) comprising:
   a. amplifying a nucleic acid comprising a non-repetitive, multicopy locus, the locus having copies on at least 2 chromosomes and a sequence that shares at least 80% sequence identity over a stretch of 80 base pairs to a nucleic acid sequence of SEQ ID NO.1 or SEQ ID NO.52 to produce an amplification product;
   b. detecting the amplification product;
   c. quantifying the amplification product; and
   d. determining the CNV of the quantified amplification product.

5. The method according to claim 1, wherein at least 4 different copies of the multicopy locus are amplified.

6. The method according to claim 2, wherein at least 4 different copies of the multicopy locus are amplified.

7. The method according to claim 3, wherein at least 4 different copies of the multicopy locus are amplified.

8. The method according to claim 4, wherein at least 4 different copies of the multicopy locus are amplified.

9. The method according to claim 1, wherein the amplifying is a non-isothermal amplifying.

10. The method according to claim 2, wherein the amplifying is a non-isothermal amplifying.

11. The method according to claim 3, wherein the amplifying is a non-isothermal amplifying.

12. The method according to claim 4, wherein the amplifying is a non-isothermal amplifying.

13. The method according to claim 1, wherein the amplifying is an isothermal amplifying.

14. The method according to claim 2, wherein the amplifying is an isothermal amplifying.

15. The method according to claim 3, wherein the amplifying is an isothermal amplifying.

16. The method according to claim 4, wherein the amplifying is an isothermal amplifying.

17. The method according to claim 1, wherein the amplifying is selected from the group consisting of quantitative real-time PCR (rtPCR), ligase chain reaction (LCR), strand displacement amplification (SDA), multiple displacement amplification (MDA), roHingcircle amplification (RCA), loop mediated isothermal amplification (LAMP), transcription mediated amplification (TMA), helicase-dependent amplification (HDA), smart-amplification process (SMAP), single primer isothermal amplification (SPIA), nicking enzyme amplification reaction (NEAR), exponential amplification reaction (EXPAR), recombinase polymerase amplification (RPA), and nucleic acid sequence based amplification (NASBA).

18. The method according to claim 2, wherein the amplifying is selected from the group consisting of quantitative real-time PCR (rtPCR), ligase chain reaction (LCR), strand displacement amplification (SDA), multiple displacement amplification (MDA), roHingcircle amplification (RCA), loop mediated isothermal amplification (LAMP), transcription mediated amplification (TMA), helicase-dependent amplification (HDA), smart-amplification process (SMAP), single primer isothermal amplification (SPIA), nicking enzyme amplification reaction (NEAR), exponential amplification reaction (EXPAR), recombinase polymerase amplification (RPA), and nucleic acid sequence based amplification (NASBA).

19. The method according to claim 3, wherein the amplifying is selected from the group consisting of quantitative real-time PCR (rtPCR), ligase chain reaction (LCR), strand displacement amplification (SDA), multiple displacement amplification (MDA), roHingcircle amplification (RCA), loop mediated isothermal amplification (LAMP), transcription mediated amplification (TMA), helicase-dependent amplification (HDA), smart-amplification process (SMAP), single primer isothermal amplification (SPIA), nicking enzyme amplification reaction (NEAR), exponential amplification reaction (EXPAR), recombinase polymerase amplification (RPA), and nucleic acid sequence based amplification (NASBA).

20. The method according to claim 4, wherein the amplifying is selected from the group consisting of quantitative real-time PCR (rtPCR), ligase chain reaction (LCR), strand displacement amplification (SDA), multiple displacement amplification (MDA), roHingcircle amplification (RCA), loop mediated isothermal amplification (LAMP), transcription mediated amplification (TMA), helicase-dependent amplification (HDA), smart-amplification process (SMAP), single primer isothermal amplification (SPIA), nicking enzyme amplification reaction (NEAR), exponential amplification reaction (EXPAR), recombinase polymerase amplification (RPA), and nucleic acid sequence based amplification (NASBA).

21. The method according to claim 17, wherein the amplifying is a helicase-dependent amplification.

22. The method according to claim 18, wherein the amplifying is a helicase-dependent amplification.

23. The method according to claim 19, wherein the amplifying is a helicase-dependent amplification.

24. The method according to claim 20, wherein the amplifying is a helicase-dependent amplification.

25. The method according to claim 17, wherein the amplifying is real-time PCR (rtPCR).

26. The method according to claim 18, wherein the amplifying is real-time PCR (rtPCR).

27. The method according to claim 19, wherein the amplifying is real-time PCR (rtPCR).

28. The method according to claim 20, wherein the amplifying is real-time PCR (rtPCR).

29. The method according to claim 1, wherein the amplification product is between 60 base pairs and 200 base pairs long.

30. The method according to claim 2, wherein the amplification product is between 60 base pairs and 200 base pairs long.

31. The method according to claim 3, wherein the amplification product is between 60 base pairs and 200 base pairs long.

32. The method according to claim 4, wherein the amplification product is between 60 base pairs and 200 base pairs long.

33. The method according to claim 1, wherein the amplifying comprises amplifying with primers that have a nucleotide sequence that differs from SEQ ID NO. 2, 3, 5, 6, 8, 9, 10, 11, and/or 12 by no more than 5 nucleotides over a stretch of 18 nucleotides.

34. The method according to claim 2, wherein the amplifying comprises amplifying with primers that have a nucleotide sequence that differs from SEQ ID NO. 2, 3, 5, 6, 8, 9, 10, 11, and/or 12 by no more than 5 nucleotides over a stretch of 18 nucleotides.

35. The method according to claim 3, wherein the amplifying comprises amplifying with primers that have a nucleotide sequence that differs from SEQ ID NO. 2, 3, 5, 6, 8, 9, 10, 11, and/or 12 by no more than 5 nucleotides over a stretch of 18 nucleotides.

36. The method according to claim 4, wherein the amplifying comprises amplifying with primers that have a nucleotide sequence that differs from SEQ ID NO. 2, 3, 5, 6, 8, 9, 10, 11, and/or 12 by no more than 5 nucleotides over a stretch of 18 nucleotides.

37. The method according to claim 1, wherein the amplification product shares at least 95% sequence identity over a stretch of 80 base pairs to a nucleic acid sequence of SEQ ID NO.1 or SEQ ID NO.52.

38. The method according to claim 2, wherein the amplification product shares at least 95% sequence identity over a stretch of 80 base pairs to a nucleic acid sequence of SEQ ID NO.1 or SEQ ID NO.52.

39. The method according to claim 3, wherein the amplification product shares at least 95% sequence identity over a stretch of 80 base pairs to a nucleic acid sequence of SEQ ID NO. 1 or SEQ ID NO.52.

40. The method according to claim 4, wherein the amplification product shares at least 95% sequence identity over a stretch of 80 base pairs to a nucleic acid sequence of SEQ ID NO.1 or SEQ ID NO.52.

* * * * *

SEQUENCE LISTING

<160> NUMBER OF SEQ ID NOS: 54

<210> SEQ ID NO 1
<211> LENGTH: 2000
<212> TYPE: DNA
<213> ORGANISM: Homo sapiens

<400> SEQUENCE: 1

```
tcaacaggcc accgtgaggg aggagctggg ccgcacgcgg gctgctggga ggcaggcagg      60
gacttggccc cgagaggccg ccgtgggggc aagagctggg cctggagagg ccctgggag     120 gcaagggcgg ggcctgcaga ggctgttctc caaccagtgc tagaactgta caggccacca    180
ggaggcagga ggtgggccct cagagcttgg ctggagaaag ttcggggcct acaaaggcgg    240
ttgggagctg ggcaggagtt gagccaaaag agcttgctta cttgctggga ggcagggccg    300
ggagagcccg acttcaggac aacttggggcc tgcggcagtc gccgggaggc ccaaccttgg    360
cgtggaggag cccaccgacc ggagaccatt tggggcctgg agatgccatc ggagggcagg    420
agctcatcct ggagaggcca ccgtgaggcc tgacctgggc ctggggagct tggcttgagg    480
aagctgtggg ccgaccaagg ccgccaggag atgggtaggc actgagtcca aagaggttgt    540
tgagaggcag gaatcgggcc tggagaccca accaggaaga agagctgggc ccggagagaa    600
tgcacggagg gtgcaagtgg gtctggagag gccgacttga ggaggttctg ggcccggaga    660
ggccgccgga agggaaaaac tgggcctgga aaggccgttg tcaggaatga gccccatggg    720
cctgaagagg ccactggcag gcgggagctg ggcctgccga agcggccgag aggcaggagc    780
tttggactcg ggaggccgca gtgaagcaac agctagctgg gcgtggagag tccgctgtga    840
ggcagaggct gggcctgtgc aggccttcgg gaggcaggag gctgggcctt gtcgaggcct    900
gcagaggcca ccgaaagtca aaagcggggc ttgggaaggc cgccgggagg catgagctgg    960
gctgggccga aagaggccac tgggaggcag gaggagctgg gcctgagag gctgccaaaa   1020 ggcaggagct tcgcctgagg atgccacagt gagacaccat ctgggtctgg agggtccact   1080
gtgaggcaga ggctgacctg tagagtccga cagtagacag aagttgggca aaagcctgat   1140
ttgaggaagt tttgggcttc aagagtcagc cacgaggcag gcactaggcc tggaaatggc   1200
ctcacagtca tgagttgggc ctaaatgggc cactgtgagg gaggagctgt gcctgttgag   1260
gctgctggca ggcaggcaga aatttggcct ggggcagctg ccatgaggca agagctgggc   1320
ctggaaaaag cccctgggag gcaagagcag ggcctgcaga ggctgttctc aagtcaaagc   1380
tgggcctgtt gatgccaccg ggaagcagaa ggtgggcctg gagagtttga cttgaggaag   1440
ttttgggcct acattggccg ccatgagctg gacaggaact gggccaaaaa aggctgttgt   1500
gaggcagcag ttgtgcctgt agacccagcc aagaggaaga ggtgggtctg gagaagcccc   1560
catgaggcag aggttgggcc tgtagacgct gacaggaggc aggagctggg cctggacagg   1620
tcaacttgag gagattttgg gccttcatag gccaccagga ggcagtagtt gggactagag   1680
agtctgactt gagtaagttt tgggcccgga gatgacgtcc tgggacagga gttgggcgtg   1740
gagaggccac cgtgaggcat aagctggatg tagagaggcc agtgtgaggc aagacctggg   1800
cctgtctagg ctgctgggag acaggcagga atctggccag ggaaggttgc catgagacaa   1860
aagttgggcc tggaaaggcc cttgtgaagc atgagcttgg cctaaagagg ccactgggtg   1920
gcaggagctg ggtgtgtaga agctgctgaa aggttgggag cttggcttgg ggggtccaca   1980
gtgaggtaga tgctgggcgt                                                2000
```

```
<210> SEQ ID NO 2
<211> LENGTH: 24
<212> TYPE: DNA
<213> ORGANISM: Homo sapiens

<400> SEQUENCE: 2
agtgggtctg gagaggccga cttg                                              24

<210> SEQ ID NO 3
<211> LENGTH: 23
<212> TYPE: DNA
<213> ORGANISM: Homo sapiens

<400> SEQUENCE: 3
tcaggcccat ggggctcatt cct                                               23

<210> SEQ ID NO 4
<211> LENGTH: 21
<212> TYPE: DNA
<213> ORGANISM: Homo sapiens

<400> SEQUENCE: 4
ttctgggccc ggagaggccg c                                                 21

<210> SEQ ID NO 5
<211> LENGTH: 27
<212> TYPE: DNA
<213> ORGANISM: Homo sapiens

<400> SEQUENCE: 5
gcagaaggtg ggcctggaga gtttgac                                           27

<210> SEQ ID NO 6
<211> LENGTH: 27
<212> TYPE: DNA
<213> ORGANISM: Homo sapiens

<400> SEQUENCE: 6
ccttttttgg cccagttcct gtccagc                                           27

<210> SEQ ID NO 7
<211> LENGTH: 30
<212> TYPE: DNA
<213> ORGANISM: Homo sapiens

<400> SEQUENCE: 7
ggaagttttg ggcctacatt ggccgccatg                                        30

<210> SEQ ID NO 8
<211> LENGTH: 20
<212> TYPE: DNA
<213> ORGANISM: Homo sapiens

<400> SEQUENCE: 8
aaggtgggcc tggagagttt                                                   20

<210> SEQ ID NO 9
<211> LENGTH: 22
<212> TYPE: DNA
<213> ORGANISM: Homo sapiens

<400> SEQUENCE: 9
ccttttttgg cccagttcct gt                                                22
```

```
<210> SEQ ID NO 10
<211> LENGTH: 24
<212> TYPE: DNA
<213> ORGANISM: Homo sapiens

<400> SEQUENCE: 10
aagttttggg cctacattgg ccgc                                          24

<210> SEQ ID NO 11
<211> LENGTH: 47
<212> TYPE: DNA
<213> ORGANISM: Artificial Sequence
<220> FEATURE:
<223> OTHER INFORMATION: Scorpion probe
<220> FEATURE:
<221> NAME/KEY: misc_feature
<223> OTHER INFORMATION: -dabcyl-C18- between position 28 and 29

<400> SEQUENCE: 11
cgagctcagt tgtgcctgta gagctcgacc tcttcctctt ggctggg                 47

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
ccgggaagca gaaggtgg                                                 18

<210> SEQ ID NO 13
<211> LENGTH: 110
<212> TYPE: DNA
<213> ORGANISM: Homo sapiens

<400> SEQUENCE: 13
agtgggtctg gagaggccga cttgaggagg ttctgggccc ggagaggccg ccggaaggga   60
aaaactgggc ctggaaaggc cgttgtcagg aatgagcccc atgggcctga              110

<210> SEQ ID NO 14
<211> LENGTH: 110
<212> TYPE: DNA
<213> ORGANISM: Homo sapiens

<400> SEQUENCE: 14
agtgggtctg gagaggccga cttgaggagg ttctgggccc ggagaggccg ccggaaggga   60
aaaactgggc ctggaaaggc cgttgtcagg aatgagcccc atgggcctga              110

<210> SEQ ID NO 15
<211> LENGTH: 110
<212> TYPE: DNA
<213> ORGANISM: Homo sapiens

<400> SEQUENCE: 15
agtgggtctg gagaggccga cttgaggagg ttctgggccc ggagaggccg ccggaaggga   60
aaaactgggc ctggaaaggc cgttgtcagg aatgagcccc atgggcctga              110

<210> SEQ ID NO 16
<211> LENGTH: 110
<212> TYPE: DNA
<213> ORGANISM: Homo sapiens
```

<400> SEQUENCE: 16
agtgggtctg gagaggccga cttgaggagg ttctgggccc ggagaggccg ccggaaggga      60
aaaactgggc ctggaaaggc cgttgtcagg aatgagcccc atgggcctga                110

<210> SEQ ID NO 17
<211> LENGTH: 110
<212> TYPE: DNA
<213> ORGANISM: Homo sapiens

<400> SEQUENCE: 17
agtgggtctg gagaggccga cttgaggagg ttctgggccc ggagaggccg ctggaaggga      60
aaaactgggc ctggaaaggc cgttgtcagg aatgagcccc atgggcctga                110

<210> SEQ ID NO 18
<211> LENGTH: 110
<212> TYPE: DNA
<213> ORGANISM: Homo sapiens

<400> SEQUENCE: 18
agtgggtctg gagaggccga cttgaggagg ttctgggccc ggagaggccg ccggaaggga      60
aaaactgggc ctggaaaggc tgttgtcagg aatgagcccc atgggcctga                110

<210> SEQ ID NO 19
<211> LENGTH: 110
<212> TYPE: DNA
<213> ORGANISM: Homo sapiens

<400> SEQUENCE: 19
agtgggtctg gagaggccga cttgaggagg ttctgggccc ggagaggccg ccggaaggga      60
aaaactgggc ctggaaaggc cgttgtgagg aatgagcccc atgggcctga                110

<210> SEQ ID NO 20
<211> LENGTH: 110
<212> TYPE: DNA
<213> ORGANISM: Homo sapiens

<400> SEQUENCE: 20
agtgggtctg gagaggccga cttgaggagg ttctgggccc ggagaggccg ccggaaggga      60
aaaactgggc ctggaaaggc cgttgtgagg aatgagcccc atgggcctga                110

<210> SEQ ID NO 21
<211> LENGTH: 110
<212> TYPE: DNA
<213> ORGANISM: Homo sapiens

<400> SEQUENCE: 21
agtgggtctg gagaggccga cttgaggagg ttctgggccc ggagaggccg ccggaaggga      60
aaaactgggc ctggaaaggc cgttgtgagg aatgagcccc atgggcctga                110

<210> SEQ ID NO 22
<211> LENGTH: 110
<212> TYPE: DNA
<213> ORGANISM: Homo sapiens

<400> SEQUENCE: 22
agtgggtctg gagaggccga cttgaggagg ttctgggccc ggagaggcca ccggaaggga      60
aaaactgggc ctggaaaggc cgttgtgagg aatgagcccc atgggcctga                110

```
<210> SEQ ID NO 23
<211> LENGTH: 110
<212> TYPE: DNA
<213> ORGANISM: Homo sapiens

<400> SEQUENCE: 23
agtgggtctg gagaggccga cttgaggagg ttctgggccc ggagaggccg ccggaaggga      60
aaaactgggc ctggaaaggt tgttgtgagg aatgagcccc atgggcctga               110

<210> SEQ ID NO 24
<211> LENGTH: 110
<212> TYPE: DNA
<213> ORGANISM: Homo sapiens

<400> SEQUENCE: 24
agtgggtctg gagaggccga cttgaggagg ttctgggccc ggagaggccg ccggaaggga      60
aaaactgggc ctagaaaggc cgttgtgagg aatgagcccc atgggcctga               110

<210> SEQ ID NO 25
<211> LENGTH: 110
<212> TYPE: DNA
<213> ORGANISM: Homo sapiens

<400> SEQUENCE: 25
agtgggtctg gagaggccga cttgaggagg ttctgggccc ggagaggccg ccggaaggga      60
aaaactgggc ctggaaaggc tgttgtgagg aatgagcccc atgggcctga               110

<210> SEQ ID NO 26
<211> LENGTH: 110
<212> TYPE: DNA
<213> ORGANISM: Homo sapiens

<400> SEQUENCE: 26
agtgggtctg gagaggccga cttgaggagg ttctgggtcc gcagaggccg ccggaaggga      60
aaaactgggc ctggaaaggc cgttgtgagg aatgagcccc atgggcctga               110

<210> SEQ ID NO 27
<211> LENGTH: 110
<212> TYPE: DNA
<213> ORGANISM: Homo sapiens

<400> SEQUENCE: 27
agtgggtctg gagaggccga cttgaggagc ttctgggccc ggagaggccg ccggaaggga      60
aaaactgggc ctggaaaggc cgttgtgagg aatgagcccc atgggcctga               110

<210> SEQ ID NO 28
<211> LENGTH: 110
<212> TYPE: DNA
<213> ORGANISM: Homo sapiens

<400> SEQUENCE: 28
agtgggtctg gagaggccga cttgaggagc ttctgggccc ggagaggccg ccggaaggga      60
aaaactgggc ctggaaaggc cgttgtgagg aatgagcccc atgggcctga               110

<210> SEQ ID NO 29
<211> LENGTH: 110
<212> TYPE: DNA
<213> ORGANISM: Homo sapiens

<400> SEQUENCE: 29
```

```
agtgggtctg gagaggccga cttgaggagc ttctgggccc ggagaggccg ccggaaggga    60
aaaactgggc ctggaaaggc cgttgtgagg aatgagcccc atgggcctga              110
```

<210> SEQ ID NO 30
<211> LENGTH: 110
<212> TYPE: DNA
<213> ORGANISM: Homo sapiens

<400> SEQUENCE: 30

```
agtgggtctg gagaggccga cttgaggagc ttctgggccc ggagaggccg ccggaaggga    60
aaaactgggc ctggaaaggc cgttgtgagg aatgagcccc atgggcctga              110
```

<210> SEQ ID NO 31
<211> LENGTH: 110
<212> TYPE: DNA
<213> ORGANISM: Homo sapiens

<400> SEQUENCE: 31

```
agtgggtctg gagaggccga cttgaggagc ttctgggccc ggagaggccg ccggaaggga    60
aaaactgggc ctggaaaggc cgttgtgagg aatgagcccc atgggcctga              110
```

<210> SEQ ID NO 32
<211> LENGTH: 110
<212> TYPE: DNA
<213> ORGANISM: Homo sapiens

<400> SEQUENCE: 32

```
agtgggtctg gagaggccga cttgaggagc ttctgggccc ggagaggccg ccggaaggga    60
aaaactgggc ctggaaaggc cgttgtgagg aatgagcccc atgggcctga              110
```

<210> SEQ ID NO 33
<211> LENGTH: 110
<212> TYPE: DNA
<213> ORGANISM: Homo sapiens

<400> SEQUENCE: 33

```
agtgggtctg gagaggccga cttgaggagc ttctgggccc ggagaggccg ccggaagaga    60
aaaactgggc ctggaaaggc cgttgtgagg aatgagcccc atgggcctga              110
```

<210> SEQ ID NO 34
<211> LENGTH: 110
<212> TYPE: DNA
<213> ORGANISM: Homo sapiens

<400> SEQUENCE: 34

```
agtgggtctg gagaggccga cttgaagagc ttctgggccc ggagaggccg ccggaaggga    60
aaaactgggc ctcgaaaggc cgttgtgagg aatgagcccc atgggcctga              110
```

<210> SEQ ID NO 35
<211> LENGTH: 110
<212> TYPE: DNA
<213> ORGANISM: Homo sapiens

<400> SEQUENCE: 35

```
agtgggtctg gagaggccga cttgaggagc ttctgggccc ggagaggccg ccggaaggga    60
aaaactgggc cggaaaggc cgttgtgagg aatgagcccc atgggcctga               110
```

<210> SEQ ID NO 36
<211> LENGTH: 110

<212> TYPE: DNA
<213> ORGANISM: Homo sapiens

<400> SEQUENCE: 36
agtgggtctg gagaggccga cttgaggagc ttctgggccc ggagaggccg ccggacggga    60
aaaactgggc cgggaaaggc cgttgtgagg aatgagcccc atgggcctga              110

<210> SEQ ID NO 37
<211> LENGTH: 110
<212> TYPE: DNA
<213> ORGANISM: Homo sapiens

<400> SEQUENCE: 37
agtgggtctg gagaggccga cttgaggagc ttctgggccc ggagaggccg ccggaaggga    60
aaaactgggc cgggaaaggc cgttgtgagg aatgagcccc atgggcctga              110

<210> SEQ ID NO 38
<211> LENGTH: 110
<212> TYPE: DNA
<213> ORGANISM: Homo sapiens

<400> SEQUENCE: 38
agtgggtctg gagaggccga cttgaggagc ttctgggccc ggagaggccg ccggaaggga    60
aaaactgggc cgggaaaggc cgttgtgagg aatgagcccc atgggcctga              110

<210> SEQ ID NO 39
<211> LENGTH: 110
<212> TYPE: DNA
<213> ORGANISM: Homo sapiens

<400> SEQUENCE: 39
agtgggtctg gagaggccga cttgaggagc ttctgggccc ggagaggccg ccggacggga    60
aaaactgggc tgggaaaggc cgttgtgagg aatgagcccc atgggcctga              110

<210> SEQ ID NO 40
<211> LENGTH: 110
<212> TYPE: DNA
<213> ORGANISM: Homo sapiens

<400> SEQUENCE: 40
agtgggtctg gagaggccga cttgaggagc ttctgggccc ggagaggccg ccggaaggga    60
aaaactgggc cgggaaaggc cgttgtgagg aatgagcccc atgggcctga              110

<210> SEQ ID NO 41
<211> LENGTH: 110
<212> TYPE: DNA
<213> ORGANISM: Homo sapiens

<400> SEQUENCE: 41
agtgggtctg gagaggccga cttgaggagc ttctgggccc ggagaggccg ccggaaggga    60
aaaactgggc cgggaaaggc cgttgtgagg aatgagcccc atgggcctga              110

<210> SEQ ID NO 42
<211> LENGTH: 146
<212> TYPE: DNA
<213> ORGANISM: Homo sapiens

<400> SEQUENCE: 42
acctcttcct cttggctggg tctacaggca caactgctgc ctcacaacag ccttttttgg    60

```
cccagttcct gtccagctca tggcggccaa tgtaggccca aaacttcctc aagtcaaact    120
ctccaggccc accttctgct tcccgg                                         146

<210> SEQ ID NO 43
<211> LENGTH: 146
<212> TYPE: DNA
<213> ORGANISM: Homo sapiens

<400> SEQUENCE: 43
acctcttcct cttggctggg tctacaggca caactgctgc ctcacaacag ccttttttgg    60
cccagttcct gtccagctca tggcggccaa tgtaggccca aaacttcctc aagtcaaact    120
ctccaggccc accttctgct tcccgg                                         146

<210> SEQ ID NO 44
<211> LENGTH: 146
<212> TYPE: DNA
<213> ORGANISM: Homo sapiens

<400> SEQUENCE: 44
acctcttcct cttggctggg tctacaggca caactgctgc ctcacaacag ccttttttgg    60
cccagttcct gtccagctca tggcggccaa tgtaggccca aaacttcctc aagtcaaact    120
ctccaggccc accttctgct tcccgg                                         146

<210> SEQ ID NO 45
<211> LENGTH: 146
<212> TYPE: DNA
<213> ORGANISM: Homo sapiens

<400> SEQUENCE: 45
acctcttcct cttggctggg tctacaggca caactgctgc ctcacaacag ccttttttgg    60
cccagttcct gtccagctca tggcggccaa tgtaggccca aaacttcctc aagtcaaact    120
ctccaggccc accttctgct tcccgg                                         146

<210> SEQ ID NO 46
<211> LENGTH: 146
<212> TYPE: DNA
<213> ORGANISM: Homo sapiens

<400> SEQUENCE: 46
acctcttcct cttggctggg tctacaggca caactgctgc ctcacaacag ccttttttgg    60
cccagttcct gtccagctca tggcggccaa tgtaggccca aaacttcctc aagtcaaact    120
ctccaggccc accttctgct tcccag                                         146

<210> SEQ ID NO 47
<211> LENGTH: 146
<212> TYPE: DNA
<213> ORGANISM: Homo sapiens

<400> SEQUENCE: 47
acctcttcct cttggctggg tctacaggca caactgctgc ctcacaacag ccttttttgg    60
cccagttcct gtccagctca tggcggccaa tgtaggccca aaacttcctc aagtcaaact    120
ctccaggccc accttctgct tcccgg                                         146

<210> SEQ ID NO 48
<211> LENGTH: 146
<212> TYPE: DNA
<213> ORGANISM: Homo sapiens
```

<400> SEQUENCE: 48

```
acctcttcct cttggctggg tctacaggca caactgctgc ctcacaacag cctttttttgg     60
cccagttcct gtccagctca tggcggccaa tgtaggccca aaacttcctc aagtcaaact    120
ctccaggccc accttctgct tcccgg                                         146
```

<210> SEQ ID NO 49
<211> LENGTH: 146
<212> TYPE: DNA
<213> ORGANISM: Homo sapiens

<400> SEQUENCE: 49

```
acctcttcct cttggctggg tctacaggca caactgctgc ctcacaacag cctttttttgg     60
cccagttcct gtccagctca tggcggccaa tgtaggccca aaacttcctc aagtcaaact    120
ctccaggccc accttctgct tcccgg                                         146
```

<210> SEQ ID NO 50
<211> LENGTH: 146
<212> TYPE: DNA
<213> ORGANISM: Homo sapiens

<400> SEQUENCE: 50

```
acctcttcct cttggctggg tctacaggca caactgctgc ctcacaacag cctttttttgg     60
cccagttcct gtccagctca tggcggccaa tgtaggccca aaacttcctc aagtcaaact    120
ctccaggccc accttctgct tcccgg                                         146
```

<210> SEQ ID NO 51
<211> LENGTH: 146
<212> TYPE: DNA
<213> ORGANISM: Homo sapiens

<400> SEQUENCE: 51

```
acctcttcct cttggctggg tctacaggca caactgctgc ctcacaacag cctttttttgg     60
cccagttcct gtccagctaa tggcggccaa tgtaggccca aaacttcctc aagtcaaact    120
ctccaggccc accttctgct tcccgg                                         146
```

<210> SEQ ID NO 52
<211> LENGTH: 5553
<212> TYPE: DNA
<213> ORGANISM: Homo sapiens

<400> SEQUENCE: 52

```
tcaacaggcc accgtgaggg aggagctggg ccgcacgcgg gctgctggga ggcaggcagg     60
gacttggccc cgagaggccg ccgtgggggc aagagctggg cctggagagg ccctgggag    120
gcaagggcgg ggcctgcaga ggctgttctc caaccagtgc tagaactgta caggccacca   180
ggaggcagga ggtgggccct cagagcttgg ctggagaaag ttcggggcct acaaaggcgg   240
ttgggagctg gcaggagtt gagccaaaag agcttgctta cttgctggga ggcagggccg    300
ggagagcccg acttcaggac aacttgggcc tgcggcagtc gccggaggc ccaaccttgg    360
cgtggaggag cccaccgacc ggagaccatt tggggcctgg agatgccatc ggagggcagg   420
agctcatcct ggagaggcca ccgtgaggcc tgacctgggc ctggggagct tggcttgagg   480
aagctgtggg ccgaccaagg ccgccaggag atgggtaggc actgagtcca aagaggttgt   540
tgagaggcag gaatcgggcc tggagaccca accaggaaga agagctgggc ccggagagaa   600
```

```
tgcacggagg gtgcaagtgg gtctggagag gccgacttga ggaggttctg ggcccggaga    660
ggccgccgga agggaaaaac tgggcctgga aaggccgttg tcaggaatga gccccatggg    720
cctgaagagg ccactggcag gcgggagctg ggcctgccga agcggccgag aggcaggagc    780
tttggactcg ggaggccgca gtgaagcaac agctagctgg gcgtggagag tccgctgtga    840
ggcagaggct gggcctgtgc aggccttcgg gaggcaggag gctgggcctt gtcgaggcct    900
gcagaggcca ccgaaagtca aaagcggggc ttgggaaggc cgccgggagg catgagctgg    960
gctgggccga agaggccac tgggaggcag gaggagctgg gcctggagag gctgccaaaa   1020
ggcaggagct cgcctgagg atgccacagt gagacaccat ctgggtctgg agggtccact   1080
gtgaggcaga ggctgacctg tagagtccga cagtagacag aagttgggca aaagcctgat   1140
ttgaggaagt tttgggcttc aagagtcagc cacgaggcag gcactaggcc tggaaatggc   1200
ctcacagtca tgagttgggc ctaaatgggc cactgtgagg gaggagctgt gcctgttgag   1260
gctgctggca ggcaggcaga aatttggcct ggggcagctg ccatgaggca agagctgggc   1320
ctggaaaaag cccctgggag gcaagagcag ggcctgcaga ggctgttctc aagtcaaagc   1380
tgggcctgtt gatgccaccg ggaagcagaa ggtgggcctg gagagtttga cttgaggaag   1440
ttttgggcct acattggccg ccatgagctg gacaggaact gggccaaaaa aggctgttgt   1500
gaggcagcag ttgtgcctgt agacccagcc aagaggaaga ggtgggtctg gagaagcccc   1560
catgaggcag aggttgggcc tgtagacgct gacaggaggc aggagctggg cctggacagg   1620
tcaacttgag gagattttgg gccttcatag gccaccagga ggcagtagtt gggactagag   1680
agtctgactt gagtaagttt tgggcccgga gatgacgtcc tgggacagga gttgggcgtg   1740
gagaggccac cgtgaggcat aagctggatg tagagaggcc agtgtgaggc aagacctggg   1800
cctgtctagg ctgctgggag acaggcagga atcggccag ggaaggttgc catgagacaa   1860
aagttgggcc tggaaaggcc cttgtgaagc atgagcttgg cctaaagagg ccactgggtg   1920
gcaggagctg ggtgtgtaga agctgctgaa aggttgggag cttggcttgg ggggtccaca   1980
gtgaggtaga tgctgggcgt gaagaatctg ctgtgaggca gacgttggga ctgtagaggc   2040
tgacgggagg cagaggctgg gcctggaggg gccaccaaga tgcaggagct gggcctggag   2100
aggctgcaaa gaagcatgac ctgggcctgg tgaggtcgac ttgagaaagt tcagggcctg   2160
gagagaaggc tgggaggcag gagctgggtc taaagaggcc attgtaacga tggagctgtg   2220
cctgtggagg ctgttgtgag gcagtagcct catctgtgga ggctgccgtg acgtagggta   2280
tgggcctaaa taggccattg tgagtcatga tcttggtctg tagaggctga ctggagaaag   2340
ttctgggcct ggagaggctg ccgggaggta ggagctgggc aaaagatgt aagcacattt   2400 gcatttatta ggcactttat ttccattatt acactgtaat atataataaa ataatcatag   2460
aactcaccat aatgtagaat cagtgggcgt gttaagcttg ttttcctgca actggatggt   2520
cccacctgag cgtgatggga gaaagtaaca gatcaatagg tattagattc tcataaggac   2580
ggcgcaacct tgatccctca catgcacggt tcacaacagg gtgcgttctc ctatgagaat   2640
ctaacgctgc tgctcatctg agaaggtgga gctcaggcgg gaatgtgagc aaaggggagt   2700
ggctgtaaat acagacgaag cttccctcac tccctcactc gacaccgctc acctcctgct   2760
gtgtggctcc ttgcggctcc atggctcagg ggttgggac ccctgctcaa gtgcatccaa   2820
agcgacccct tcccacaccag tcttcacagt ggtcaagggc agcaaccact tagctcccaa   2880
ggcatgtgcc tcagctggca tttcgtcaca atcaacagta agtggtagct tgagtcactg   2940
tgaggtcacc tactggaaat caccagcatc ccatttccca ctggcaaaga gctcagcgct   3000
```

```
gcccccctggg aaaccaaacc tatgcccaaa tcccatctgt gtgggtgtat ctcctgggac    3060
ccttcctaac atattagtca gagtccaatc aggaagcata aaccactcaa aagtttaaag    3120
tggtaaaatt taatacagag aattattcat tataacaggt gaacagcata atgagagatt    3180
ggctagcaca aagtaaagag aactctagag aatataggac tagcccaggc caggcatggt    3240
ggctcaggcc tgaaattcca gcaatttgag aagctaatgc aggaggattg cttaaggcca    3300
ggagctagag accggtctgg acaacagagt gagaccctgt ctctatccaa agaagaaaa     3360 aagttagctg gtggtggtag tgcacacttg cagtcccagc tactcggaat gcggaagttt    3420
gagcctggga ggtcaaggct gcagtgaggc atgattatgc cactacagtc cagcctggtg    3480
acagagcaag accctgtctc aaagaacaaa acaacaacaa ccatttacag acagaaaaga    3540
aatagagcta ataagctgag gaaagatgtt gaaatgtgac aagtaaagta acatgaggtc    3600
ttttgtctat ttaaaataat caaacaaaaa atgacttact aaattataat accctgtgct    3660
ggcaaaggtg cagtgaaatg ggcacttcct tatactatga gaggtggtta aattgtgtat    3720
aagccttccc gggtaaagcc tgtcaatttt ttaaaataat ggagacaggg tctcaccata    3780
ctgccatact gcctcctcca actcttggcc tcaagcaatc ctcctctctt agcctcccaa    3840
agtgctaaga ttatagctgg gaggcaccca aaaccctgtc aatttacatc aagggtaagg    3900
agaatgtcca ttcaccatga ctcacagtaa tcttacttct ggggagacaa ttcagtctaa    3960
acaaaaggtc atctgtacac acacagtaaa aatctgggag taactgaaga cagagttggt    4020
aagtgaaata agaaacagtt ataagaaatt aaactatggt atcaataggc acctggtaca    4080
aaaggtcagt tgatgttggc tgctactttt ttgttgtttt gagacagggt ctcactctgt    4140
cacccaggct ggagtgcaga ggcctgatca tgactcactg cagtctcagc ctccctgggc    4200
tcaagtgatc ctcccacctc agcctcccaa gtagctggga ctacaggaac atgccaccac    4260
actaggctaa ttcatgtatt tttctgtagg gatggtgact cccccttgt ttccaaggcc     4320 tatcgcaaac tcttggcctc gagccatcct cctgcctcag cctcccaaag tgttgcgatt    4380
accagtgtga gccaccacac ctggccagct gctactttta tcaatattat tcttattcca    4440
ctcaattaaa aattattatt ttcaaggcta tgcaacagta tgtatcctac agcgtaattg    4500
taaaaacata tacagtcgtc gtccctcagt atacagaatt agttccagcc ccccatctct    4560
gcatatacca aaatccatgc ttactcacgt ttcgctgtca cccctctgga atccacgtat    4620
acgaaaattc caaatattag ttgggcatag tggcaagcac ctgtagtctc agccacgtgg    4680
gaggttgagg tgggaggatc gcttcagcct ggaaggttga ggctgcagtc agctgcgata    4740
gcactactac actccagcct tggacaacag agggagaccc tgtctcagaa caaaaaaaaa    4800
taaaaaataa aaaataaaac aggttagaaa ctgtgatgag gtctgctggg caaaattcca    4860
tataagcaaa gtataaatta ataaagcaaa tcgtgataaa ttagtacgat tgactttctg    4920
gagtttctga caataaaagt aaggaaaatg cagaacacaa agacagagag taaaagagaa    4980
aattaggaaa gcattctaca tgttgaatag gaagacactg gccatgttcg tgcagcggca    5040
gtatgtcgtg acatgacata ccttggagag aagttaacag atgaggaagt tgataaaaat    5100
catcagagaa gcaaaatact ggtagggaca ctcagtaaaa ccatgaaatt tccataactt    5160
atgtcagcaa agtgggaata ttgtacagtg tgtgttgaag ttcctataca acattgttta    5220
tctgcctttt gtttgtttgt aaggaatgta catactaaaa gttcttcttg ctgtcaaaag    5280
aatatgtgtg aataagtcat tttaacttat tcttctgttt ttcttttatc ttcctgccat    5340
```

```
catcccacag ccttacttta gaaatttttt ttttagaaaa ttgaacaagt gctccttgtg    5400
gtggcacatg cctcgaggat gggaggcagg ggtggaaggg tcacttgagg ccattagttt    5460
gacaccagcc tggccaacaa agtgagaccc cgtgtctaca aaacaattta aaaattagcc    5520
aagtatcatc atgtatacct acagtcccag cta                                5553

<210> SEQ ID NO 53
<211> LENGTH: 44
<212> TYPE: DNA
<213> ORGANISM: Homo sapiens
<220> FEATURE:
<221> NAME/KEY: misc_feature
<222> LOCATION: (27)..(28)
<223> OTHER INFORMATION: Spacer

<400> SEQUENCE: 53
ccgcgttggg agcttggctt ggcgcggatc tacctcactg tgga                    44

<210> SEQ ID NO 54
<211> LENGTH: 20
<212> TYPE: DNA
<213> ORGANISM: Homo sapiens

<400> SEQUENCE: 54
aggagatttt gggccttcat                                               20
```